United States Patent
Matsumoto et al.

(10) Patent No.: US 7,662,380 B2
(45) Date of Patent: Feb. 16, 2010

(54) ZAQ LIGAND-1 ANTIBODIES AND USES THEREOF

(75) Inventors: Hirokazu Matsumoto, Tsukuba (JP); Yasuko Horikoshi, Tsukuba (JP); Yasushi Masuda, Tsukuba (JP); Tetsuya Ohtaki, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 545 days.

(21) Appl. No.: 10/542,664

(22) PCT Filed: Jan. 21, 2004

(86) PCT No.: PCT/JP2004/000498

§ 371 (c)(1),
(2), (4) Date: Apr. 11, 2006

(87) PCT Pub. No.: WO2004/065419

PCT Pub. Date: Aug. 5, 2004

(65) Prior Publication Data
US 2006/0217536 A1 Sep. 28, 2006

(30) Foreign Application Priority Data
Jan. 22, 2003 (JP) .............................. 2003-014055

(51) Int. Cl.
*A61K 39/395* (2006.01)
*C12N 5/12* (2006.01)
(52) U.S. Cl. ................. 424/141.1; 424/139.1; 435/326; 435/346
(58) Field of Classification Search ........................ None
See application file for complete search history.

(56) References Cited

U.S. PATENT DOCUMENTS

| | | | | |
|---|---|---|---|---|
| 6,485,938 | B1* | 11/2002 | Sheppard et al. | ........... 435/69.1 |
| 7,045,299 | B2* | 5/2006 | Ohtaki et al. | ................ 435/7.1 |
| 2002/0115610 | A1* | 8/2002 | Zhou et al. | ..................... 514/12 |
| 2002/0172678 | A1 | 11/2002 | Ferrara et al. | |
| 2002/0192634 | A1 | 12/2002 | Ferrara et al. | |
| 2007/0014799 | A1* | 1/2007 | Matsumoto et al. | ...... 424/145.1 |

FOREIGN PATENT DOCUMENTS

| JP | 2004-043468 | 2/2004 |
|---|---|---|
| WO | WO 01/16309 A1 | 3/2001 |
| WO | WO 02/00711 A2 | 1/2002 |
| WO | WO 02/06483 A1 | 1/2002 |
| WO | WO 02/36625 A2 | 5/2002 |
| WO | WO 03/066860 A1 | 8/2003 |

OTHER PUBLICATIONS

Score sequence search: "20071029_120952_us-542-664-1.rapbm", Published Applications database, p. 1-11.*
Christiansen et al (Mol Cancer Ther, 2004, 3:1493-1501).*
Topp et al (Journal of Controlled Release, 1998, 53:15-23).*
Tockman et al (Cancer Res., 1992, 52:2711s-2718s).*
Johnstone and Thorpe (Immunochemistry in Practice, 2nd Ed., 1987, Blackwell Scientific Publications, Oxford, pp. 49-50).*
Lecouter, J., et al., "EG-VEGF and the Concept of Tissue-Specific Angiogenic Growth Factors", Seminars in *Cell & Developmental Biology*, (2002), vol. 13, pp. 3-8.
Lecouter, J., et al., "Endocrine Gland-Derived VEGF and the Emerging Hypothesis of Organ-Specific Regulation of Angiogenesis", *Nature Medicine*, (2002), vol. 8, No. 9, pp. 913-917.
Lecouter, J., et al., "Identification of an Angiogenic Mitogen Selective for Endocrine Gland Endothelium", *Nature*, (2001), vol. 412, pp. 877-884.
Li, M., et al., "Identification of Two Prokineticin cDNAs: Recombinant Proteins Potently Contract Gastrointestinal Smooth Muscle", *Molecular Pharmacology*, (2001), vol. 59, No. 4, pp. 692-698.
EBI Database, Database Accession No. Q8TC69, Database UniProt, (2002), XP-002366641.
Masuda, Y., et al., "Isolation and Identification of EG-VEGF/Prokineticins as Cognate Ligands for Two Orphan G-Protein-Coupled Receptors", *Biochemical and Biophysical Research Communications*, (2002), vol. 293, No. 1, pp. 396-402.
R. Lin, et al., "Characterization of Endocrine Gland-derived Vascular Endothelial Growth Factor Signaling in Adrenal Cortex Capillary Endothelial Cells", The Journal of Biological Chemistry, (2002), pp. 8724-8729, vol. 277, No. 10.

* cited by examiner

*Primary Examiner*—Laura B Goddard
(74) *Attorney, Agent, or Firm*—Foley & Lardner LLP

(57) ABSTRACT

The antibody of the present invention has an extremely high binding ability to human ZAQL-1, can neutralize the activity of human ZAQL-1, and inhibits the action of human ZAQL-1. Therefore, the antibody is useful as a preventive or therapeutic agent or a diagnostic agent for, e.g., digestive diseases, diseases associated with angiogenesis, diseases relating to pregnancy, eating disorders, sleeping disorders, seasonal depression, reproductive dysfunction, endocrine diseases, senile dementia, Alzheimer's disease, various disorders caused by aging, cerebral circulatory disorders, head trauma, spinal injury, epilepsy, anxiety, depression, manic depression, schizophrenia, alcoholism, Parkinson's disease, hypertension, arteriosclerosis, arrhythmia, premenstral syndrome, glaucoma, cancer, AIDS, diabetes, etc.

6 Claims, 11 Drawing Sheets

ZAQ LIGAND-1 ANTIBODIES AND USES THEREOF

This application is the National Phase filing of International Patent Application No. PCT/JP2004/000498, filed Jan. 21, 2004, which claims priority to JP 2003/014055, filed Jan. 22, 2003.

TECHNICAL FIELD

The present invention relates to a novel antibody having a binding specificity for a polypeptide comprising the amino acid sequence represented by SEQ ID NO: 1 or SEQ ID NO: 2, or a salt thereof. More particularly, the present invention relates to a method of quantifying the polypeptide or a salt thereof, based on an antigen-antibody reaction, antibodies useful for developing agents for the diagnosis and prevention/treatment of diseases associated with the polypeptide or a salt thereof, utilizing the neutralizing activity, and so on.

BACKGROUND ART

Human ZAQ ligand-1 (a polypeptide having the amino acid sequence represented by SEQ ID NO: 1 or SEQ ID NO: 2) (hereinafter sometimes briefly referred to as human ZAQL-1) is a ligand for the ZAQ receptor and is a peptide having the ileum contractile action (WO 02/06483). Also, human Bv8 mature peptide (hereinafter sometimes briefly referred to as human ZAQL-2), which is a mammalian peptide of frog Bv8 having a similar structure to that of human ZAQ ligand-1, activates MAP kinase and PI-3 kinase to exert a neuroprotective action (Eur. J. Neuroscience, 13, 1694, 2001). Subsequently, these peptides were reported also as novel peptides, prokineticin-1 (PK-1) and prokineticin-1 (PK-2) found through the DNA database (Mol. Pharmacol., 59, 692, 2001).

It is reported that human ZAQL-1 as an endocrine tissue-specific endocrine gland-derived vascular endothelial growth factor (EG-VEGF) takes part in the formation of highly permeable endothelial structure having a high permeability (fenestration), which characterizes the endocrine tissue, and that the recognition site of hypoxia-inducible factor-1 (HIF-1) involved in expression induction under hypoxic conditions is present in the transcription regulatory region of human ZAQL-1 gene to induce gene expression under hypoxic conditions (Nature, 412, 877, 2001).

To further clarify the physiological function of human ZAQL-1, a simple and high-sensitivity assay system for detecting/quantifying human ZAQL-1 has been earnestly desired.

DISCLOSURE OF THE INVENTION

The present inventors have made extensive studies to solve the foregoing problems and as a result, have developed an immunoassay method for specifically detecting human ZAQL-1 with a high sensitivity, which comprises producing a plurality of monoclonal antibodies using human ZAQL-1 as an antigen and using the monoclonal antibodies in combinations. Thus, changes of human ZAQL-1 in biological components such as blood, cerebrospinal fluid, urine, etc. can be assayed in a simple manner with a high sensitivity.

That is, the present invention provides the following features and so on.

(1) A monoclonal antibody specifically reacting with a polypeptide comprising the amino acid sequence represented by SEQ ID NO: 1 or SEQ ID NO: 2, or a salt thereof.

(2) The monoclonal antibody according to (1), which specifically reacts with a polypeptide consisting of the amino acid sequence represented by SEQ ID NO: 1, or a salt thereof.

(3) The monoclonal antibody according to (1), which specifically reacts with a peptide comprising at least one member selected from the amino acids at positions 8-9, 11, 15, 17, 21, 23, 25-28, 30, 34, 36-37, 39-40, 44-46, 48, 52-53, 55, 64, 66, 68, 70-73, 75-76 and 78-86 in the amino acid sequence represented by SEQ ID NO: 1 or SEQ ID NO: 2.

(4) The monoclonal antibody according to (1), which does not recognize a polypeptide having the amino acid sequence represented by SEQ ID NO: 3.

(5) The monoclonal antibody according to (1), which is labeled.

(6) The monoclonal antibody according to (1), which is represented by ZL1-107a producible from a hybridoma represented by ZL1-107 (FERM BP-8256).

(7) The monoclonal antibody according to (1), which is represented by ZL1-234a producible from a hybridoma represented by ZL1-234 (FERM BP-8257).

(8) The monoclonal antibody according to (1), which has an activity of neutralizing a peptide having the amino acid sequence represented by SEQ ID NO: 1 or SEQ ID NO: 2.

(9) A pharmaceutical comprising the monoclonal antibody according to (1).

(10) The pharmaceutical according to (9), which is an agent for preventing/treating endometrial cancer, endometriosis or ovulation disorders.

(11) A diagnostic agent comprising the monoclonal antibody according to (1).

(12) The diagnostic agent according to (11), which is a diagnostic agent for endometrial cancer, endometriosis or ovulation disorders.

(13) A diagnostic agent comprising the monoclonal antibody according to (1).

(14) A method of quantifying a polypeptide comprising the amino acid sequence represented by SEQ ID NO: 1 or SEQ ID NO: 2, or a salt thereof, which comprises using the monoclonal antibody according to (1).

(15) A method of diagnosis for a disease associated with a polypeptide comprising the amino acid sequence represented by SEQ ID NO: 1 or SEQ ID NO: 2, or a salt thereof, which comprises using the monoclonal antibody according to (1).

(16) The method of diagnosis according to (15), wherein the disease is endometrial cancer, endometriosis or ovulation disorders.

(17) A method of quantifying a polypeptide comprising the amino acid sequence represented by SEQ ID NO: 1 or SEQ ID NO: 2, or a salt thereof, which comprises competitively reacting the monoclonal antibody according to (1) with a test fluid and a labeled polypeptide comprising the amino acid sequence represented by SEQ ID NO: 1 or SEQ ID NO: 2, or a salt thereof, and determining a ratio of the labeled polypeptide bound to the antibody, or a salt thereof.

(17a) A method of quantifying a polypeptide comprising the amino acid sequence represented by SEQ ID NO: 1 or SEQ ID NO: 2, or a salt thereof, which comprises reacting the monoclonal antibody according to (1) immobilized on a carrier, a labeled form of the monoclonal antibody according to (1) (an antibody different from the monoclonal antibody immobilized on a carrier described above) and a test fluid and then determining the activity of marker.

(18) A method of quantifying a polypeptide comprising the amino acid sequence represented by SEQ ID NO: 1 or SEQ ID NO: 2, or a salt thereof, which comprises:

(a) reacting the monoclonal antibody according to (6) immobilized on a carrier, a labeled form of the monoclonal antibody according to (7) and a test fluid, and then assaying the activity of marker, or, (b) reacting the monoclonal antibody according to (7) immobilized on a carrier, a labeled form of the monoclonal antibody according to (6) and a test fluid, and then assaying the activity of marker.

(19) A hybridoma producing the monoclonal antibody according to (1).

(20) The hybridoma according to (19), which is represented by ZL1-107 (FERM BP-8256) or ZL1-234 (FERM BP-8257).

(21) A method of producing the monoclonal antibody according to (6) or (7), which comprises culturing the hybridoma according to (19) in vivo or in vitro and collecting the monoclonal antibody according to (6) or (7) from the body fluid or culture.

(22) A method of preventing/treating endometrial cancer, endometriosis or ovulation disorders, which comprises administering an effective dose of the monoclonal antibody according to (1) to a mammal.

(23) Use of the monoclonal antibody according to (1) to manufacture an agent for preventing/treating endometrial cancer, endometriosis or ovulation disorders.

BEST MODE FOR CARRYING OUT THE INVENTION

Figure 1:
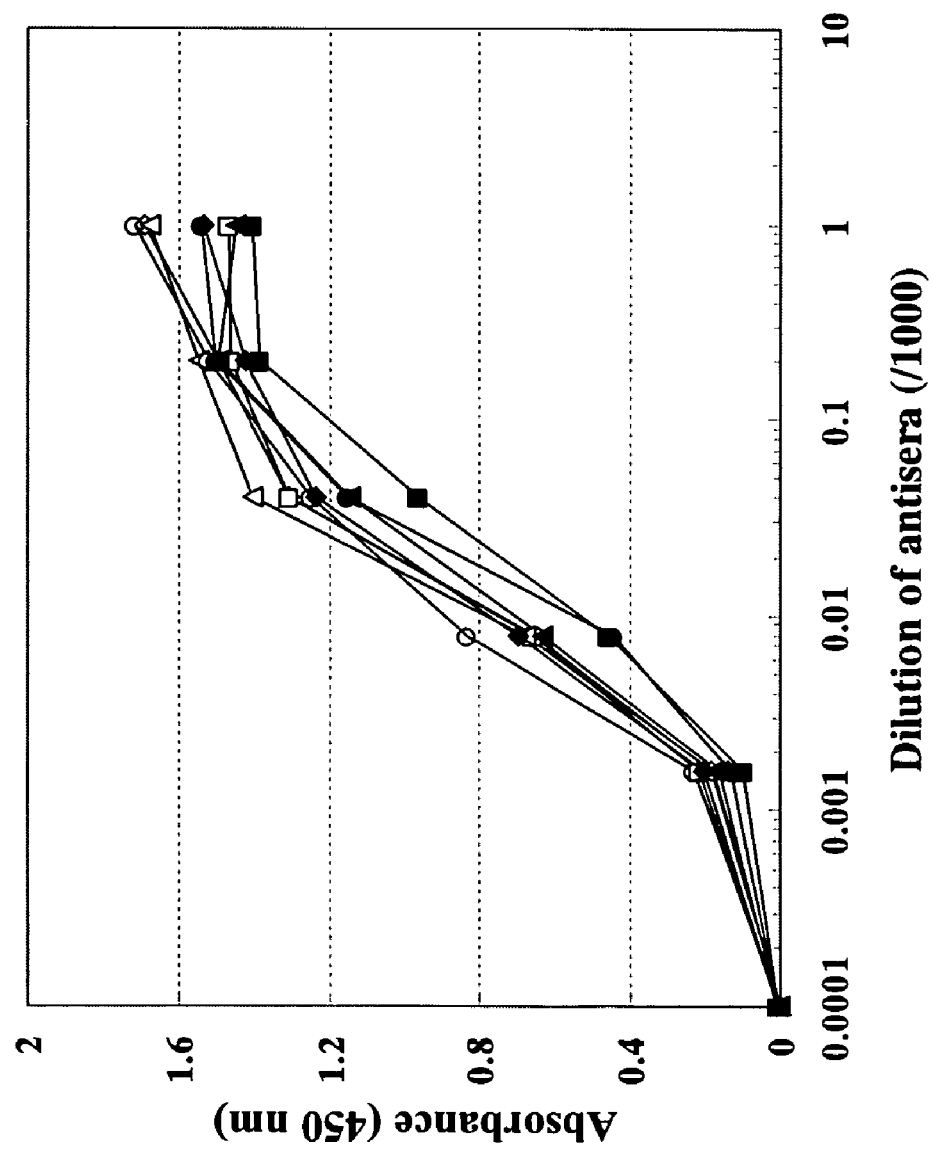
FIG. 1 shows the assay results of antibody titer in antisera of mice immunized with human ZAQL-1-BTG complex. In the figure, -◇- (-open diamond-) represents mouse No. 1, -□- (-open square-) represents mouse No. 2, -△- (-open triangle-) represents mouse No. 3, -○- (-open circle-) represents mouse No. 4, -◆- (-closed diamond-) represents mouse No. 5, -■- (-closed square) represents mouse No. 6, -▲- (-closed triangle-) represents mouse No. 7 and -●- (-solid circle-) represents mouse No.8.
Figure 2:
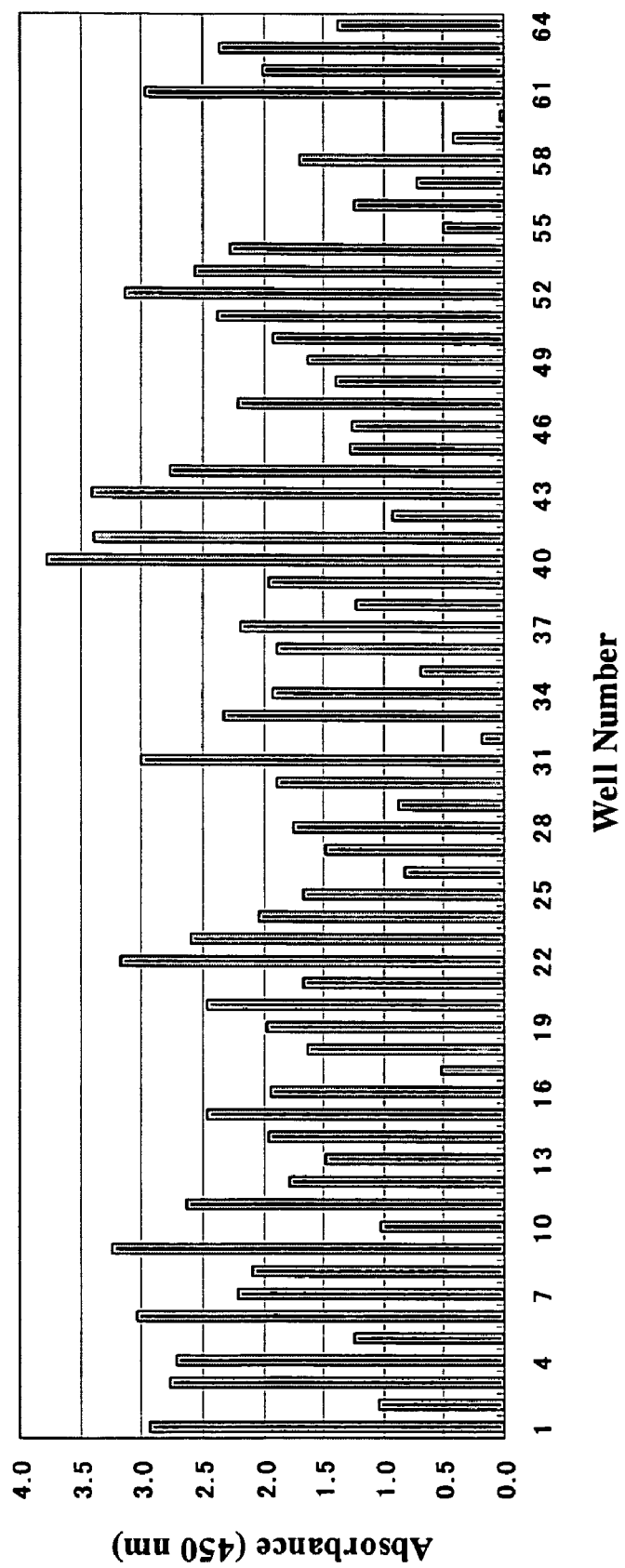
FIG. 2 shows the conditions in which hybridomas derived from mice immunized with the human ZAQL-1-BTG complex produced antibodies (results of absorption spectrometry).
Figure 3:
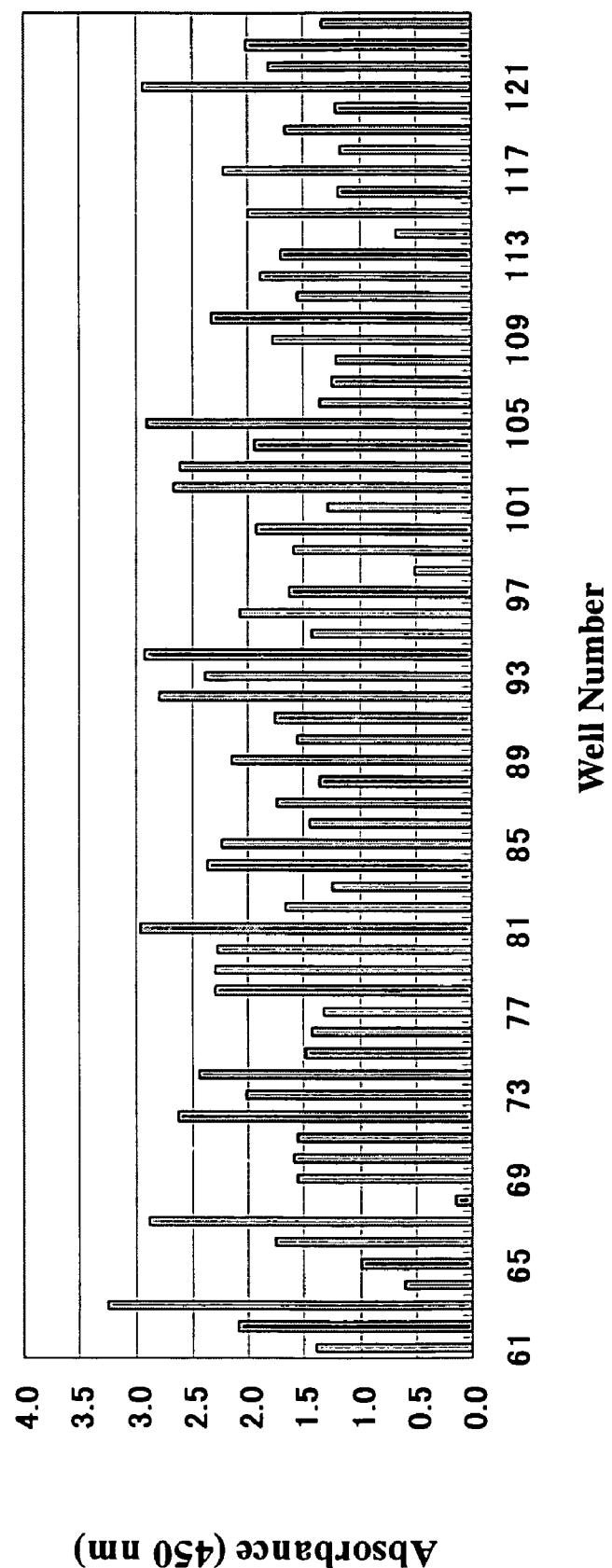
FIG. 3 shows the conditions in which hybridomas derived from mice immunized with the human ZAQL-1-BTG complex produced antibodies (results of absorption spectrometry).
Figure 4:
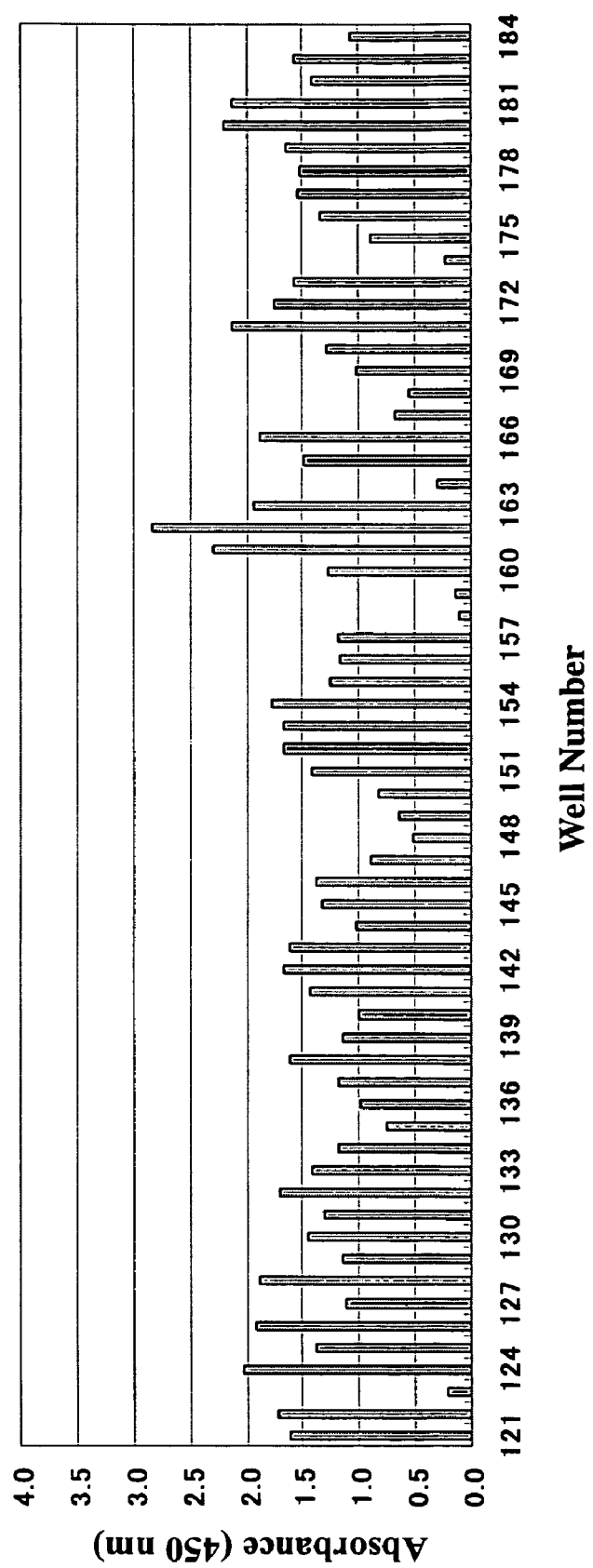
FIG. 4 shows the conditions in which hybridomas derived from mice immunized with the human ZAQL-1-BTG complex produced antibodies (results of absorption spectrometry).
Figure 5:
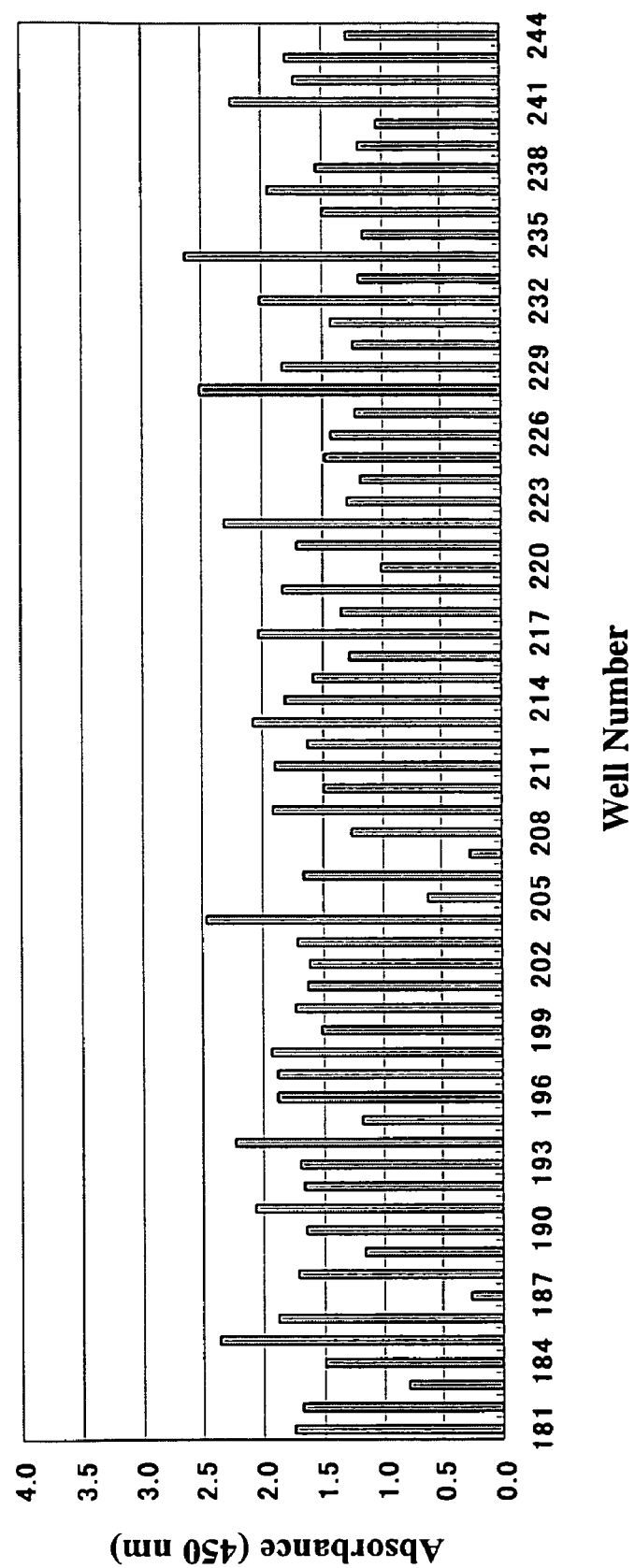
FIG. 5 shows the conditions in which hybridomas derived from mice immunized with the human ZAQL-1-BTG complex produced antibodies (results of absorption spectrometry).

Throughout the specification, the proteins (polypeptides) are represented in accordance with the conventional way of describing peptides, that is, the N-terminus (amino terminus) at the left hand and the C-terminus (carboxyl terminus) at the right hand. In the protein used in the present invention including the polypeptide having the amino acid sequence represented by SEQ ID NO: 1, the C-terminus may be in any form of a carboxyl group, a carboxylate, an amide and an ester.

As the polypeptides comprising the amino acid sequence represented by SEQ ID NO: 1 or SEQ ID NO: 2, there are used polypeptides having the amino acid sequence represented by SEQ ID NO: 1 or SEQ ID NO: 2, wherein several (1 to 5) amino acids are added to the amino acid sequence described above; those wherein several (1 to 5) amino acids are inserted into the amino acid sequence described above, those wherein several (1 to 5) amino acids in the amino acid sequence described above are replaced with other amino acids, and the like.

As salts of the polypeptide comprising the amino acid sequence represented by SEQ ID NO: 1 or SEQ ID NO: 2, salts with physiologically acceptable acids (e.g., inorganic acids or organic acids), bases (e.g., alkali metal salts), etc. may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Examples of the monoclonal antibody of the present invention, which specifically reacts with the polypeptide comprising the amino acid sequence represented by SEQ ID NO: 1 or SEQ ID NO: 2 or salts thereof (hereinafter sometimes referred to as the antibody of the present invention), are monoclonal antibodies which specifically react with the polypeptide having the amino acid sequence represented by SEQ ID NO: 1 or SEQ ID NO: 2, or a salt thereof, etc., preferably a polypeptide having the amino acid sequence represented by SEQ ID NO: 1, or a salt thereof, etc.

Preferably, the antibody of the present invention specifically reacts with a peptide comprising at least one (preferably about 3 to about 6) members selected from the amino acids at positions 8-9, 11, 15, 17, 21, 23, 25-28, 30, 34, 36-37, 39-40, 44-46, 48, 52-53, 55, 64, 66, 68, 70-73, 75-76 and 78-86 in the amino acid sequence represented by SEQ ID NO: 1 or SEQ ID NO: 2. In addition, the antibody of the present invention does not recognize a polypeptide having the amino acid sequence represented by SEQ ID NO: 3.

More preferably, the antibody of the present invention is an antibody that neutralizes the activity of a polypeptide having the amino acid sequence represented by SEQ ID NO: 1 or SEQ ID NO: 2.

Specific examples include a monoclonal antibody shown by ZL1-107a or ZL1-234a, and the like.

Methods of preparing antigen for the antibody of the present invention and methods of manufacturing the antibody are described below.

(1) Preparation of Antigen

To prepare the antibody of the present invention, any antigen such as (synthetic) peptides having 1 or 2 more antigenic determinants, which are the same as in the polypeptide comprising the amino acid sequence represented by SEQ ID NO: 1 or SEQ ID NO: 2, or a salt thereof, etc. may be used (hereinafter these antigens are sometimes merely referred to as the human ZAQL-1 antigen).

The polypeptide comprising the amino acid sequence represented by SEQ ID NO: 1 or SEQ ID NO: 2, or a salt thereof can be produced by some modifications of publicly known methods, e.g., the method described in WO 02/06483. They may also be (a) prepared from mammalian tissue or cells of human, simian, rat, mouse, etc., by publicly known methods or with modifications, (b) chemically synthesized by publicly known peptide synthesis methods using a peptide synthesizer, etc., or (c) produced by culturing a transformant bearing a DNA encoding a polypeptide comprising amino acid represented by SEQ ID NO:1 or SEQ ID NO:2, or a salt thereof.

(a) Where the human ZAQL-1 antigen is prepared from the mammalian tissues or cells, the tissues or cells are homogenized, then extracted with an acid, an alcohol, etc., and the extract is purified and isolated by a combination of salting-out, dialysis, gel filtration, chromatography techniques such as reverse phase chromatography, ion exchange chromatography, affinity chromatography and the like.

(b) Where the human ZAQL-1 antigen is prepared chemically, the synthetic peptides used are, for example, a peptide having the same structure as the human ZAQL-1 antigen purified from natural one, a peptide containing 1 or 2 more amino acid sequences, which are the same amino acid sequences consisting of at least 3, preferably at least 6 amino acids in an optional region of the amino acid sequence represented by SEQ ID NO: 1 or SEQ ID NO: 2, etc.

(c) Where the polypeptide comprising the amino acid sequence represented by SEQ ID NO:1 or SEQ ID NO:2, or a salt thereof are produced using the DNA-bearing transformants, the DNA can be produced in accordance with publicly known cloning techniques [e.g., the method described in Molecular Cloning (2nd ed., J. Sambrook et al., Cold Spring Harbor Lab. Press, 1989), etc.]. The cloning techniques include (1) a method in which transformants containing DNAs encoding the polypeptide comprising the amino acid sequence represented by SEQ ID NO:1 or SEQ ID NO:2, or a salt thereof are obtained from cDNA library by hybridization using DNA probes or DNA primers designed based on the amino acid sequence of the polypeptide comprising the amino acid sequence represented by SEQ ID NO:1 or SEQ ID NO:2, or a salt thereof, or (2) a method in which transformants containing DNAs encoding the polypeptide comprising the amino acid sequence represented by SEQ ID NO:1 or SEQ ID NO:2, or a salt thereof are obtained by PCR using DNA primers designed based on the amino acid sequence of the polypeptide comprising the amino acid sequence represented by SEQ ID NO:1 or SEQ ID NO:2, or a salt thereof, etc.

Peptides used as the human ZAQL-1 antigen can be prepared (1) by peptide synthesis methods publicly known, or (2) by cleaving a polypeptide comprising the amino acid sequence represented by SEQ ID NO:1 or SEQ ID NO:2 with an appropriate peptidase.

For the methods for peptide synthesis, for example, any of solid phase synthesis and liquid phase syntheses may be used. That is, the partial peptides or amino acids that can construct the peptide are condensed with the remaining part. Where the product contains protecting groups, these protecting groups are removed to give the desired peptide. Publicly known methods for condensation and removal of the protecting groups are methods described below.

(i) M. Bodanszky & M. A. Ondetti: Peptide Synthesis, Interscience Publishers, New York (1966)

(ii) Schroeder & Luebke: The Peptide, Academic Press, New York (1965)

After the reaction, the product may be purified and isolated by a combination of conventional purification methods such as solvent extraction, distillation, column chromatography, liquid chromatography, recrystallization, etc. to give the peptide. When the peptide obtained by the above methods is in a free form, the peptide can be converted into an appropriate salt by a publicly known method; conversely when the peptide is obtained in a salt form, it can be converted into a free form by a publicly known method.

Amides of the peptide may be obtained using commercially available resins for peptide synthesis, which are suitable for formation of the amides. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenylacetamidomethyl resin, polyacrylamide resin, 4-(2',4'-dimethoxyphenylhydroxymethyl) phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective peptide according to various condensation methods publicly known in the art. At the end of the reaction, the peptide is cut out from the resin and at the same time, the protecting groups are removed to obtain the objective peptide. Alternatively, the objective peptide may also be obtained by protecting the peptide in part with chlorotrityl resin, oxime resin, 4-hydroxybenzoic acid type resin, etc., and removing the protective groups from the taken out peptide in a conventional manner.

For condensation of the protected amino acids described above, a variety of activation reagents for peptide synthesis may be used, and carbodiimides are particularly preferable. Examples of such carbodiimides include DCC, N,N'-diisopropylcarbodiimide, N-ethyl-N'-(3-dimethylaminoprolyl) carbodiimide, etc. For activation by these reagents, the protected amino acids in combination with a racemization inhibitor (e.g., HOBt, HOOBt) are added directly to the resin, or the amino acids previously protected in the form of symmetric acid anhydrides, HOBt esters or HOOBt esters are activated, followed by adding the thus activated protected amino acids to the resin. Solvents suitable for use to activate the protected amino acids or condense with the resin may be appropriately chosen from solvents known to be usable for peptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; tertiary amines such as pyridine, etc.; ethers such as dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to peptide bond-forming reactions and is usually selected in the range of approximately $-20°$ C. to $50°$ C. The activated amino acid derivatives are used generally in an excess of about 1.5 to about 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel adverse effects on the subsequent reactions.

Examples of the protecting groups used to protect the amino groups in the starting amino acids include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc. Examples of the protecting groups for carboxyl groups include a $C_{1-6}$ alkyl group, $C_{3-8}$ cycloalkyl group, a $C_{7-14}$ aralkyl group, 2-adamantyl, 4-nitrobenzyl, 4-methoxybenzyl, 4-chlorobenzyl, phenacyl, benzyloxycarbonyl hydrazide, trityl hydrazide, or the like.

The hydroxyl group of serine and threonine can be protected through, for example, its esterification or etherification. Examples of the groups suitable for the esterification include a lower ($C_{1-6}$) alkanoyl group, such as acetyl group, etc.; an aroyl group such as benzoyl group, etc., and a group derived from carbonic acid such as benzyloxycarbonyl group, ethoxycarbonyl group, etc. Examples of a group suitable for the etherification include benzyl group, tetrahydropyranyl group, t-butyl group, etc.

Examples of groups for protecting the phenolic hydroxyl group of tyrosine include Bzl, Cl-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, Bom, Bum, Boc, Trt, Fmoc, etc.

Examples of the activated carboxyl groups in the starting compounds include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino acids, in which the amino groups are activated in the starting material, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrofluoric acid, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia; or the like. The elimination of the protecting groups by the acid treatment described above is carried out generally at a temperature of approximately $-20°$ C. to $40°$ C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups and activation of the functional groups involved in the reaction may be appropriately chosen from publicly known groups and publicly known means.

In another method for obtaining the amides of the peptide, for example, the α-carboxyl group of the carboxy terminal amino acid is first protected by amidation; the peptide chain is then extended to a desired length toward the amino group side. Thereafter, a peptide in which only the protecting group of the N-terminal α-amino group in the peptide chain has been eliminated from the peptide and a peptide (or amino acids) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are eliminated by the method described above to give the desired crude peptide. This crude peptide is purified by various known purification means. Lyophilization of the major fraction gives the amide of the desired peptide.

To prepare the esterified peptide, for example, the α-carboxyl group of the carboxy terminal amino acid is condensed with a desired alcohol to prepare the amino acid ester, which is followed by procedure similar to the preparation of the amidated peptide above to give the ester form of the desired peptide.

The human ZAQL-1antigen may be provided for direct immunization in its immobilized form. The human ZAQL-1 antigen may also be bound or adsorbed to an appropriate carrier and the complex produced can be provided for immunization. A mixing ratio of the carrier to the human ZAQL-1 antigen (hapten) may be in any ratio of any type, as long as the antibody can be efficiently produced to the human ZAQL-1 antigen. A high molecular carrier conventionally used to produce an antibody to a hapten may be used in a weight ratio of 0.1 to 100 based on 1 of hapten. As such a high molecular carrier, there are used a naturally occurring high molecular carrier and a synthetic high molecular carrier. Examples of the naturally occurring high molecular carrier used are serum albumin from mammals such as bovine, rabbit, human, etc., thyroglobulins from mammals such as bovine, rabbit, etc., hemoglobins from mammals such as bovine, rabbit, human, ovine, etc or keyhole limpet KHL hemocyanin. Examples of the synthetic high molecular carrier, which can be used, are various latexes including polymers, copolymers, etc., for example, polyamino acids, polystyrenes, polyacryls, polyvinyls, polypropylenes, etc.

For coupling of the hapten and the carrier, a variety of condensing agents can be used. Examples of the condensing agents, which are advantageously employed, are diazonium compounds such as bis-diazotized benzidine capable of crosslinking tyrosines, histidines or tryptophans; dialdehyde compounds such as glutaraldehyde, etc. capable of crosslinking amino groups with each other; diisocyanate compounds such as toluene-2,4-diisocyanate, etc.; dimaleimide compounds such as N,N'-o-phenylenedimaleimide, etc. capable of crosslinking thiols with each other; maleimide activated ester compounds capable of crosslinking an amino group with a thiol group; carbodiimide compounds capable of crosslinking an amino group with a carboxyl group; etc. In the crosslinking of amino groups with each other, one amino group is reacted with an activated ester reagent (e.g., N-succinimidyl 3-(2-pyridyldithio)propionate (SPDP), etc.) having dithiopyridyl group and then reduced to introduce the thiol group, whereas another amino group is introduced with a maleimide group using a maleimide activated ester reagent, and the two groups may be reacted with each other.

(2) Preparation of Monoclonal Antibody

The human ZAQL-1 antigen is administered to warm-blooded animal either solely or together with carriers or diluents to the site where the production of antibody is possible by administration routes such as intraperitoneally, intravenously, subcutaneously, etc. In order to potentiate the antibody productivity upon the administration, complete Freund's adjuvants or incomplete Freund's adjuvants may be administered. The administration is usually carried out once in every 2 to 6 weeks and approximately 2 to 10 times in total. Examples of the warm-blooded animal are simian, rabbits, canine, guinea pigs, mice, rats, ovine, goats, fowl, etc. with mice being preferred for preparation of the monoclonal antibodies.

In preparing the monoclonal antibodies, the animal wherein the antibody titer is noted is chosen from warm-blooded animals, e.g., mice, immunized with the human ZAQL-1 antigen, then the spleen or lymph node is collected 2 to 5 days after the final immunization and antibody-producing cells contained therein are fused with myeloma cells, whereby the antibody-producing hybridomas of the present invention can be prepared. The anti-human ZAQL-1 antibody titer in antisera can be determined, for example, by reacting labeled human ZAQL-1, which will be described later, with the antiserum followed by assaying the binding activity of a marker bound to the antibody. The fusion may be operated, for example, by known methods, e.g., by the Kohler and Milstein method [Nature, 256, 495 (1975)]. Examples of fusion accelerators are polyethylene glycol (PEG), Sendai virus, etc., of which PEG is preferably employed. Examples of the myeloma cells are NS-1, P3U1, SP2/0, AP-1, etc. In particular, P3U1 or the like is preferably employed. A preferred ratio in count of the antibody-producing cells (spleen cells) to the myeloma cells used is within a range of approximately 1:1 to 20:1. When PEG (preferably, PEG 1000 to PEG 6000) is added in a concentration of approximately 10 to 80% followed by incubation generally at 20 to 40° C., preferably at 30 to 37° C. generally for 1 to 10 minutes, an efficient cell fusion can be carried out.

Various methods can be used for screening of the antibody-producing hybridomas of the present invention. Examples of such methods include a method which comprises adding the hybridoma supernatant to a solid phase (e.g., microplate) adsorbed with a polypeptide comprising the amino acid sequence represented by SEQ ID NO:1 or SEQ ID NO:2, its salts or partial peptides thereof, directly or together with a carrier, then adding an anti-immunoglobulin antibody (when mouse cells are used for the cell fusion, anti-mouse immunoglobulin antibody is used) labeled with a radioactive substance, an enzyme or the like, or Protein A and detecting the antibody of the present invention bound to the solid phase; a method which comprises adding the hybridoma supernatant to a solid phase adsorbed with an anti-immunoglobulin antibody or Protein A, adding a polypeptide comprising the amino acid sequence represented by SEQ ID NO:1 or SEQ ID NO:2, which is labeled with a radioactive substance, an enzyme, etc. and detecting the antibody of the present invention bound to the solid phase; etc. Screening and plating of the antibody of the present invention can be performed generally in a medium for animal cells (e.g., RPMI 1640) containing 10-20% fetal calf serum and supplemented with HAT (hypoxanthine, aminopterin and thymidine). The antibody titer in the hybridoma supernatant can be assayed by the same procedures as in the assay for the antibody titer of the antibody of the present invention in the antisera described above.

Separation and purification of the antibody of the present invention can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which involves collecting only the antibody with an activated adsorbent such as an antigen-binding solid phase, Protein A, Protein G, etc. and dissociating the binding to obtain the antibody; and the like].

As described above, the antibody of the present invention can be produced by culturing hybridoma cells in a warm-blooded animal in vivo or in vitro and collecting the antibody from the body fluids or the culture.

Screening can be performed for (a) the hybridomas that react with a segment (partial region) of polypeptide comprising the amino acid sequence represented by SEQ ID NO: 1 or SEQ ID NO: 2 and (b) the hybridomas that react with the polypeptide described above but do not react with a segment of the polypeptide, for example, by measuring the binding property of a peptide corresponding to the segment to an antibody produced by the hybridoma.

Hereinafter, the method of quantifying (immunoassay for) the polypeptide comprising the amino acid sequence represented by SEQ ID NO:1 or SEQ ID NO:2, or a salt thereof is described in more detail.

By using the antibody of the present invention, the polypeptide comprising the amino acid sequence represented by SEQ ID NO:1 or SEQ ID NO:2 can be assayed, or can be detected by tissue staining, etc. For these purposes, the antibody molecule itself may be used, or F(ab')2, Fab' or Fab fractions of the antibody molecule may be used.

The quantification method using the antibody of the present invention is not particularly limited, but any quantification method can be used, so long as the amount of antibody, antigen or antibody-antigen complex corresponding to the amount of antigen (e.g., the amount of human ZAQL-1) in a fluid to be tested can be detected by chemical or physical means and the amount of the antigen can be calculated from a standard curve prepared from standard solutions containing known amounts of the antigen. Advantageously used are, for example, sandwich assay, competitive assay, immunometric assay and nephrometry; in terms of sensitivity and specificity, the sandwich assay described later is particularly preferred.

(1) Sandwich Assay

After the antibody of the present invention immobilized on a carrier is reacted with a labeled form of the antibody of the present invention (which is an antibody different from the antibody of the present invention immobilized on a carrier) and a fluid to be tested, the activity of a marker is assayed to quantify a polypeptide comprising the amino acid sequence represented by SEQ ID NO:1 or SEQ ID NO:2, or a salt thereof, in the test fluid.

Preferably, the sandwich assay includes:

(i) a method for quantification of a polypeptide comprising the amino acid sequence represented by SEQ ID NO:1 or SEQ ID NO:2, or a salt thereof in a test fluid, which comprises reacting a monoclonal antibody represented by ZL1-107a, which is immobilized on a carrier, a labeled monoclonal antibody represented by ZL1-234a and the test fluid, and then assaying the activity of a marker;

(ii) a method for quantification of a polypeptide comprising the amino acid sequence represented by SEQ ID NO:1 or SEQ ID NO:2, or a salt thereof in a test fluid, which comprises reacting a monoclonal antibody represented by ZL1-234a, which is immobilized on a carrier, a labeled monoclonal antibody represented by ZL1-107a and the test fluid, and then assaying the activity of a marker; and so on.

In the sandwich assay, a test fluid is reacted with an immobilized form of the antibody of the present invention (primary reaction), then reacted with a labeled form of the antibody of the present invention (secondary reaction) and the activity of a labeling agent on the insoluble carrier is assayed; thus, the amount of polypeptide comprising the amino acid sequence represented by SEQ ID NO:1 or SEQ ID NO:2 (preferably human ZAQL-1), or a salt thereof in a test fluid can be assayed. The primary and secondary reactions may be carried out simultaneously or sequentially with intervals. The type of the labeling agent and the method of immobilization may be the same as those described hereinabove. In the immunoassay by the sandwich technique, it is not always necessary that the antibody used for the solid phase and for the labeled antibody should be one type or one species but a mixture of two or more antibodies may also be used for the purpose of improving the assay sensitivity, etc. In the sandwich assay method, where the antibody used in the primary reaction is, for example, the monoclonal antibody represented by ZL1-234a, a preferred monoclonal antibody used in the secondary reaction is the monoclonal antibody represented by ZL1-107a; where the antibody used in the primary reaction is the monoclonal antibody represented by ZL1-107a, a monoclonal antibody preferably used in the secondary reaction is the monoclonal antibody represented by ZL1-234a. Preferably, these antibodies are labeled with, e.g., horse radish peroxidase (HRP) and the labeled antibodies are provided for use.

(2) Competitive Assay

The antibody of the present invention, a test fluid and a labeled form of polypeptide comprising the amino acid sequence represented by SEQ ID NO:1 or SEQ ID NO:2, or a salt thereof are competitively reacted, and a ratio of the labeled polypeptide comprising the amino acid sequence represented by SEQ ID NO:1 or SEQ ID NO:2 bound to the antibody, or a salt thereof, is determined, thereby to quantify the polypeptide comprising the amino acid sequence represented by SEQ ID NO:1 or SEQ ID NO:2, or a salt thereof in the test fluid.

The competitive assay is performed by, e.g., a solid phase technique.

Specifically, anti-mouse IgG antibody (manufactured by ICN/CAPPEL) is used as a solid phase antibody, (i) the antibody of the present invention (e.g., ZL1-107a or ZL1-234a), (ii) a polypeptide comprising the amino acid sequence represented by SEQ ID NO: 1 or SEQ ID NO: 2, or a salt thereof, which is labeled with HRP, and (iii) a test fluid are added to a plate where the solid phase antibody is present; after the reaction, the HRP activity adsorbed onto the solid phase is assayed to quantify the polypeptide comprising the amino acid sequence represented by SEQ ID NO: 1 or SEQ ID NO: 2, or a salt thereof.

(3) Immunometric Assay

In the immunometric assay, an antigen in a test fluid and a solid phase antigen are competitively reacted with a given amount of a labeled form of the antibody of the present invention followed by separating the solid phase from the liquid phase; or an antigen in a test fluid and an excess amount of labeled form of the antibody of the present invention are reacted, then a solid phase antigen is added to bind an unreacted labeled form of the antibody of the present invention to the solid phase and the solid phase is then separated from the liquid phase. Thereafter, the labeled amount of any of the phases is measured to determine the antigen level in the test fluid.

(4) Nephrometry

In the nephrometry, the amount of insoluble sediment, which is produced as a result of the antigen-antibody reaction in a gel or in a solution, is measured. Even when the amount of an antigen in a test fluid is small and only a small amount of the sediment is obtained, a laser nephrometry utilizing laser scattering can be suitably used.

Examples of labeling agents, which are employed for the aforesaid assay methods (1) to (4) using labeling agents, are radioisotopes, enzymes, fluorescent substances, luminescent substances, lanthanides, etc. Examples of radioisotopes are $[^{125}I]$, $[^{131}I]$, $[^{3}H]$, $[^{14}C]$, etc. Preferred examples of the enzymes are those that are stable and have a higher specific activity, which include β-galactosidase, β-glucosidase, alkaline phosphatase, peroxidase, malate dehydrogenase, etc. Examples of the fluorescent substances include cyanine fluorescent dyes (e.g., Cy2, Cy3, Cy5, Cy5.5, Cy7 (manufactured by Amersham Biosciences), etc.), fluorescamine, fluorescein isothiocyanate, etc. Examples of the luminescent substances are luminol, a luminol derivative, luciferin, lucigenin, etc. Furthermore, a biotin-avidin system may be used as well for binding an antibody or antigen to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In applying each of these immunoassay techniques to the method of the present invention, it is not necessary to set any special condition, operation, etc. The assay system of the present invention may be constructed in addition to the conditions or operations conventionally used for each of the assay techniques, taking into account the technical consideration of one skilled in the art. For details of such conventional technical means, reference may be made to a variety of reviews, reference books, etc.[for example, Hiroshi Irie (ed.): "Radioimmunoassay" (published by Kodansha, 1974)]; Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)] (all published by Academic Press); etc.). Thus, where the assay system of the present invention is constructed by applying the sandwich immunoassay method, etc., its method is not limited to EXAMPLES later described.

As described above, the antibody of the present invention can quantify the polypeptide comprising the amino acid sequence represented by SEQ ID NO: 1 or SEQ ID NO: 2, or a salt thereof with high sensitivity, and is thus useful for further elucidation of the physiological functions of the polypeptide described above and for diagnosis of diseases associated with the polypeptide described above. Specifically, the level of polypeptide comprising the amino acid sequence represented by SEQ ID NO: 1 or SEQ ID NO: 2, or a salt thereof contained in a body fluid (blood, plasma, serum, urine, etc.) is determined using the antibody of the present invention, whereby diagnosis can be made for digestive diseases (e.g., enteritis, diarrhea, constipation, malabsorption syndrome, etc.), diseases associated with angiogenesis [e.g., cancers (e.g., thyroid cancer, testicular cancer, adrenal tumor, pancreatic cancer, lung cancer, kidney cancer, liver cancer, non-small cell lung cancer, ovarian cancer, prostate cancer, gastric cancer, bladder cancer, breast cancer, cervical cancer, colonic cancer, rectal cancer, endometrial cancer, etc.), polycystic ovary syndrome, ovarian hyperstimulation syndrome, etc.], diseases relating to pregnancy (e.g., toxemia of pregnancy, placental hypoplasia, threatened abortion, endometriosis, sterility, ovulation disorders, etc.), eating disorders (e.g., anorexia, bulimia nervosa, etc.), sleeping disorders [e.g., primary insomnia, circadian rhythm disorders (e.g., changes in physical conditions caused by three-shift work, time zone change syndrome (jet lag), etc.)], seasonal depression, reproductive dysfunction, endocrine diseases, senile dementia, Alzheimer's disease, various disorders caused by aging, cerebral circulatory disorders (e.g., apoplexy, etc.), head trauma, spinal injury, epilepsy, anxiety, depression, manic depression, schizophrenia, alcoholism, Parkinson's disease, hypertension, arteriosclerosis, arrhythmia, premenstral syndrome, glaucoma, cancer, AIDS, diabetes, etc. (preferably, diseases associated with angiogenesis, diseases relating to pregnancy, etc., and more preferably, endometrial cancer, endometriosis, ovulation disorders, etc.). For example, in diagnosis of polycystic ovary syndrome, the aforesaid polypeptide in a body fluid is quantified and when the level of the polypeptide is more abundant than in healthy volunteers, e.g., its blood level is about 3 fmol/ml or more, preferably about 10 fmol/ml or more, it is diagnosed that one suffers from polycystic ovary syndrome.

Furthermore, the antibody of the present invention is useful as an agent for preventing/treating diseases associated with the polypeptide comprising the amino acid sequence represented by SEQ ID NO: 1 or SEQ ID NO: 2, or a salt thereof, for example, digestive diseases (e.g., enteritis, diarrhea, constipation, malabsorption syndrome, etc.), diseases associated with angiogenesis [e.g., cancers (e.g., thyroid cancer, testicular cancer, adrenal tumor, pancreatic cancer, lung cancer, kidney cancer, liver cancer, non-small cell lung cancer, ovarian cancer, prostate cancer, gastric cancer, bladder cancer, breast cancer, cervical cancer, colonic cancer, rectal cancer, endometrial cancer, etc.), polycystic ovary syndrome, ovarian hyperstimulation syndrome, etc.], diseases relating to pregnancy (e.g., toxemia of pregnancy, placental hypoplasia, threatened abortion, endometriosis, sterility, ovulation disorders, etc.), eating disorders (e.g., anorexia, bulimia nervosa, etc.), sleeping disorders [e.g., primary insomnia, circadian rhythm disorders (e.g., changes in physical conditions caused by three-shift work, time zone change syndrome (jet lag), etc.)], seasonal depression, reproductive dysfunction, endocrine diseases, senile dementia, Alzheimer's disease, various disorders caused by aging, cerebral circulatory disorders (e.g., apoplexy, etc.), head trauma, spinal injury, epilepsy, anxiety, depression, manic depression, schizophrenia, alcoholism, Parkinson's disease, hypertension, arteriosclerosis, arrhythmia, premenstral syndrome, glaucoma, cancer, AIDS, diabetes, etc. Preferably, the antibody is an agent for preventing/treating diseases associated with angiogenesis, diseases relating to pregnancy, etc., and more preferably, an agent for preventing/treating endometrial cancer, endometriosis, ovulation disorders, etc.

The preventive/therapeutic agent comprising the antibody of the present invention is low toxic, and can be administered orally or parenterally to human or mammals (e.g., rats, rabbits, ovine, swine, bovine, feline, canine, simian, etc.) as it is in the form of liquid preparation or as a pharmaceutical composition of appropriate dosage form. The dose may vary depending on subject to be administered, target disease, conditions, route for administration, etc.; when it is used for the treatment of the adult patient with, e.g., polycystic ovary syndrome, it is advantageous to administer the antibody of the present invention parenterally to the patient through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For oral administration, the corresponding dose may be administered. When the conditions are extremely serious, the dose may be increased depending on the conditions.

The antibody of the present invention may be administered directly in its intact form or in the form of an appropriate pharmaceutical composition. The pharmaceutical composition used for the administration described above may contain the antibody of the present invention or a salt thereof, a pharmacologically acceptable carrier and a diluent or an excipient. Such a pharmaceutical composition is provided in a dosage form suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, etc. The injectable preparations may include dosage forms such as intravenous, subcutaneous, intracutaneous and intramuscular injections, drip infusions, etc. These injectable preparations may be prepared by per se known methods. For example, the injectable preparations may be prepared by dissolving, suspending or emulsifying the antibody or a salt thereof described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate dissolution aid such as an alcohol [e.g., ethanol), a polyalcohol (e.g., propylene glycol, polyethylene glycol), a nonionic surfactant (e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a dissolution aid such as benzyl benzoate, benzyl alcohol, etc. The injection thus prepared is preferably filled in an appropriate ampoule. The suppository used for rectal administration may be prepared by blending the aforesaid antibody or a salt thereof with conventional bases for suppositories.

Advantageously, the pharmaceutical compositions for oral or parenteral use described above are prepared into pharmaceutical preparations with a unit dose suited to fit a dose of the active ingredients. Such unit dose preparations include, for example, tablets, pills, capsules, injections (ampoules), suppositories, etc. The amount of the antibody contained is generally about 5 to about 500 mg per dosage unit form; it is preferred that the aforesaid antibody is contained in about 5 to about 100 mg especially in the form of injection, and in about 10 to 250 mg for the other forms.

Each composition described above may further contain other active components unless any adverse interaction is caused by formulating together with the antibody described above.

In the present specification, amino acids, etc. are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

TFA: trifluoroacetic acid
DMF: N,N-dimethylformamide
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
SPDP: N-succinimidyl 3-(2-pyridyldithio)propionate
GMBS: N-(4-maleimidobutyryloxy)succinimide
BSA: bovine serum albumin
BTG: bovine thyroglobulin
EIA: enzyme immunoassay
HPLC: reversed phase high performance liquid chromatography
HRP: horse radish peroxidase
FBS: fetal bovine serum
d-FBS: dialyzed fetal bovine serum
TMB: 3,3',5,5'-tetramethylbenzidine
H/HBSS: HEPES buffered Hanks' balanced salt solution The sequence identification numbers used in the present specification represent the amino acid sequences of the following peptides.

[SEQ ID NO: 1]

This shows the amino acid sequence of human ZAQL-1.

[SEQ ID NO: 2]

This shows the amino acid sequence of human ZAQL-1. In the amino acid sequence represented by SEQ ID NO: 1, Val at the 48 position is replaced by Ile.

[SEQ ID NO: 3]

This shows the amino acid sequence of human ZAQL-2.

Hybridoma ZL1-107 obtained in EXAMPLE 1 later described has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8256 since Dec. 9, 2002.

Hybridoma ZL1-234 obtained in EXAMPLE 1 later described has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8257 since Dec. 9, 2002.

The antibodies acquired from the respective hybridomas are shown by the cell names with suffix "a."

Hereinafter, the present invention will be described in more detail with reference to EXAMPLES but is not deemed to limit the scope of the present invention thereto.

Human ZAQL-1 (SEQ ID NO: 1) used in EXAMPLES was obtained by the method described in Reference Example 1 of WO 02/06483.

Human ZAQL-2 (SEQ ID NO: 3) used in EXAMPLES was obtained by the method described in Reference Example 1 of WO 02/62944.

EXAMPLE 1

(1) Production of Human ZAQL-1-containing Immunogen

A complex of human ZAQL-1and bovine thyroglobulin (BTG) was prepared and used as an immunogen. BTG, 10 mg, was dissolved in 1 ml of 0.02M phosphate-buffered saline (pH 6.8) containing 0.1 M sodium chloride and the solution was mixed with 100 μl of a DMF solution containing 1.86 mg of SPDP. The mixture was reacted at room temperature for 60 minutes. Further 0.19 ml of 0.1M acetate buffer (pH 4.5) containing 160 μmol of dithiothreitol was added to the reaction mixture, followed by reacting at room temperature for 30 minutes. After centrifuging at 13,000 rpm for 1 minute, the supernatant was separated on a Sephadex G-25 column (eluent: 0.1M phosphate buffer containing 2 mM EDTA, pH 6.0) to give SH-introduced BTG. Next, 50 μl of DMF containing 2.07 μmol of GMBS was added to 0.1M phosphate buffer (pH 6.8) containing 2 mg (207 nmol) of human ZAQL-1. The mixture was reacted at room temperature for 60 minutes. The reaction liquid was separated on a Sephadex G-25 column (eluent: 0.1M phosphate buffer, pH 6.7) to give maleimide-introduced human ZAQL-1. Next, 6.5 mg of the SH-introduced BTG was mixed with 1.2 mg of the maleimide-introduced antibody fraction. The resulting mixture was then reacted at 4° C. for 24 hours. After the reaction, the mixture was dialyzed to physiological saline at 4° C. for 3 days.

(2) Immunization

The human ZAQL-1-BTG complex obtained (1) above was subcutaneously immunized into BALB/C female mice of 6 to 8 weeks old with complete Freund's adjuvant in about 20 µg/animal, respectively. At every 3 other weeks following primary immunization, mice were boosted twice or thrice with the same amount of immunogen.

(3) Preparation of Horse Radish Peroxidase (HRP)-labeled Human ZAQL-1

Human ZAQL-1 was crosslinked with HRP (for enzyme immunoassay, manufactured by Boehringer Mannheim), which was used as a marker for enzyme immunoassay (EIA).

HRP, 8.5 mg (213 nmol), was dissolved in 0.02M phosphate buffer (pH 6.8) containing 0.95 ml of 0.1M sodium chloride and the solution was mixed with 50 µl of DMF solution containing 1.99 mg of SPDP. The mixture was reacted at room temperature for 60 minutes. Further 0.5 ml of 0.1M acetate buffer (pH 4.5) containing 9.25 mg of dithiothreitol was added to the reaction mixture. After reacting at room temperature for 30 minutes, the reaction mixture was separated on a Sephadex G-25 column (eluent: 2 mM EDTA-containing 0.1 M phosphate buffer, pH 6.0) to give SH-introduced HRP. Human ZAQL-1, 2 mg, was dissolved in 0.1M phosphate buffer (pH 6.7) and the solution was mixed with 50 µl of DMF solution containing 0.69 mg (2.5 µmol) of GMBS. The mixture was reacted at room temperature for 60 minutes and then separated on a Sephadex G-25 column (eluent: 0.1M phosphate buffer, pH 6.8) to give maleimide-introduced human ZAQL-1. After 1.67 mg (41.4 nmol) of the thus prepared SH-introduced HRP was mixed with 1.2 mg (124 nmol) of the maleimide-introduced human ZAQL-1 prepared above, the mixture was reacted at 4° C. for a day. After the reaction, fractionation was performed through Ultrogel AcA44 (manufactured by LKB-Pharmacia) column to give HRP-labeled human ZAQL-1.

(4) Assay for Antibody Titer of Antisera in Mice Immunized with the Human ZAQL-1-BTG Complex Mice were immunized twice with the human ZAQL-1-BTG complex with 3 weeks interval. One week after, blood was drawn from the ocular fundus to collect blood. After the blood was further centrifuged at 4° C. for 15 minutes at 12,000 rpm, the supernatant was recovered to give antisera. The antibody titer in antisera was assayed by the following method. To prepare an anti-mouse immunoglobulin antibody-bound microplate, 100 µl each of 0.1 M carbonate buffer (pH 9.6) solution containing 100 µg/ml of anti-mouse immunoglobulin antibody (IgG fraction, manufactured by Cappel) was first dispensed onto a 96-well microplate and then allowed to stand at 4° C. over 24 hours. Next, after the plate was washed with phosphate buffered saline (PBS, pH 7.4), a 300 µl aliquot of PBS containing 25% Block Ace (manufactured by Snow Brand Milk Products) was dispensed in each well and treated at 4° C. for at least 24 hours to block redundant binding sites of the well.

After 50 µl of Buffer C [0.02M phosphate buffer, pH 7.0, containing 1% BSA, 0.4M NaCl, 0.05% 2 mM EDTA-Na (disodium ethylenediamine-N,N,N',N'-tetraacetate dihydrate), DOJINDO Co.] and 100 µl of antisera to the complex diluted with Buffer C were added to each well of the obtained anti-mouse immunoglobulin antibody-bound microplate, the reaction was carried out at 4° C. for 16 hours. Next, the plate was washed with PBS and 100 µl of HRP-labeled human ZAQL-1 (diluted to 300-fold with Buffer C) prepared in (4) above was added thereto, followed by reacting at room temperature for a day. Then, the plate was washed with PBS and 100 µl of TMB Microwell Peroxidase Substrate System (KIRKEGAARD & PERRY LAB, INC., consigned to Funakoshi Co., Ltd.) was added thereto and the reaction was carried out at room temperature for 10 minutes to assay the enzyme activity on a solid phase. The reaction was terminated by adding 100 µl of 1M phosphoric acid. Absorption at 450 nm was measured with a plate reader (BICHROMATIC, manufactured by Dainippon Pharmaceutical Co., Ltd.).

The results are shown in FIG. 1.

Increased antibody titers to human ZAQL-1 were observed in the antisera to the human ZAQL-1-BTG complex with all of the eight (8) immunized mice.

(5) Production of Anti-human ZAQL-1 monoclonal Antibodies

Mice showing relatively high antibody titers received final immunization by intravenous injection with solutions of 50 to 100 µg of the immunogen in 0.2 ml of saline. After 4 days of the final immunization, the spleen was removed from mice, and spleen cells were pressed against a stainless mesh and filtered through a stainless mesh. The cells were suspended in Eagles' minimum essential medium (MEM) to give the spleen cell suspension. BALB/C mouse-derived myeloma cells P3-X63.Ag8.U1 (P3U1) were used as cells for cell fusion (Current Topics in Microbiology and Immunology, 81, 1, 1978).

The cell fusion was performed by the original method (Nature, 256, 495, 1975) with modifications.

The spleen cells and P3U1 were washed 3 times with serum-free MEM, respectively, and they were blended in a 5:1 proportion of the spleen cells to P3U1 in cell count. The cell mixture was centrifuged at 800 rpm for 15 minutes to deposit the cells. After the supernatant was thoroughly removed, the deposit was lightly unraveled and 0.3 ml of 45% polyethylene glycol (PEG) 6000 (manufactured by Kochlight) was added thereto. The mixture was allowed to stand for 7 minutes in a warm water bath of 37° C. to perform cell fusion. The fusion was followed by addition of MEM to the cells at a rate of 2 ml/min. After 15 ml of MEM in total was added, the mixture was centrifuged at 600 rpm for 15 minutes and the supernatant was removed. The cell deposit was suspended in 10% fetal calf serum-containing GIT medium (Wako Pure Chemical Industries, Ltd.) (GIT-10% FCS) in $2\times10^5$/ml of P3U1, and the suspension was plated on 192 wells of a 24-well Multidish (manufactured by Limbro) in 1 ml/well. After the plating, the cells were incubated at 37° C. in a 5% carbonic acid gas incubator. Twenty-four hours after, GIT-10% FCS medium (HAT medium) containing HAT ($1\times10^{-4}$ M hypoxanthine, $4\times10^{-7}$ M aminopterin, $1.6\times10^{-3}$ M thymidine) was added to the cells in 1 ml/well, thereby to initiate HAT selective culture. The HAT selective culture was continued by discarding 1 ml of the old medium on Days 3, 6 and 9 after start of the incubation and replenishing 1 ml of HAT medium. Growth of hybridomas was noted 9 to 14 days after the cell fusion. When the culture medium turned yellow (ca. $1\times10^6$ cells/ml), the supernatant was collected and the antibody titer was assayed in accordance with the procedure described in EXAMPLE 1 (4).

By way of examples of the selected antibody-producing cell lines of the hybridomas derived from mice immunized with the human ZAQL-1-BTG, the conditions that the hybridomas produced the antibodies are shown in FIGS. 2 through 5, using mice No. 2 and No. 3 (see FIG. 1). The following 4 hybridomas in total were selected from the antibody-producing hybridomas acquired [Table 1].

TABLE 1

| Hybridoma No. | Human ZAQL-1 Reactivity[1] | Class/Subclass | Antibody |
|---|---|---|---|
| 1 | + | IgG1, κ | ZL1-107a |
| 2 | ± | IgG1, κ | ZL1-234a |
| 3 | + | IgG2b, κ | ZL1-222a |
| 4 | − | IgG1, κ | |

[1] When 1 nM of human ZAQL-1 was present:
+: $(B/B_0) < 0.50$
±: $0.50 \leq (B/B_0) < 0.70$
−: $0.70 \leq (B/B_0)$
B: Amount of HRP-labeled human ZAQL-1 bound to the antibody in the presence of antigen
$B_0$: Amount of HRP-labeled human ZAQL-1 bound to the antibody in the presence of antigen Next, these hybridomas were cloned by the limiting dilution. In cloning, thymocytes from BALB/C mice were added as feeder cells in $5 \times 10^5$ cells/well. After cloning, the hybridomas were intraperitoneally injected to mice (BALB/C) in 1 to $3 \times 10^6$ cells/mouse, to which 0.5 ml of mineral oil had previously been given intraperitoneally. The ascites fluid containing the antibody was collected 6 to 20 days after.

The monoclonal antibody was purified through a protein A column from the ascites fluid obtained. That is, 6 to 20 ml of the ascites fluid was diluted with an equal volume of binding buffer [1.5M glycine containing 3.5M NaCl and 0.05% NaN$_3$ (pH 9.0)], and the dilution was applied on recombinant protein A-agarose (manufactured by Repligen Corporation) column, which had been previously equilibrated with the binding buffer. The specific antibody was eluted with an eluting buffer [0.1M citrate buffer containing 0.05% NaN$_3$ (pH 3.0)]. The eluate was dialyzed to PBS at 4° C. for 2 days, which was subjected to cell-free filtration through a filter of 0.22 μm (manufactured by Millipore) and then stored at 4° C. or −80° C.

In class/subclass determinations of the monoclonal antibodies, enzyme-linked immunosorbent assay (ELISA) using purified monoclonal antibody-bound solid phase was carried out. That is, 100 μl each of 0.1M carbonate buffer (pH 9.6) solution containing 2 μg/ml of the antibody was dispensed on a 96-well microplate, which was then allowed to stand at 4° C. for 24 hours. Following the procedure described above, redundant binding sites in the wells were blocked with Block Ace. Thereafter, the class and subclass of immobilized antibodies were determined by ELISA using an isotyping kit (Mouse-Typer™ Sub-Isotyping Kit, manufactured by Bio-RAD). In ZL1-222a, the H chain was IgG2b and the L chain was κ, and in all of the remainders, the H chain was IgG1 and the L chain was κ.

EXAMPLE 2

Competitive Enzyme Immunoassay

The monoclonal antibodies prepared using human ZAQL-1-BTG as an immunogen were examined for their reaction specificity according to the following method.

First, the antibody titers of respective solutions of the four monoclonal antibodies obtained were assayed by the method described in EXAMPLE 1-(5), and the antibody level wherein the binding amount of a labeled form reached about 50% of the saturation binding amount was determined as an antibody level used for the competitive assay—EIA (about 30 to 50 ng/ml). Next, each of the monoclonal antibodies was added to each well of the anti-mouse immunoglobulin antibody-bound microplate described in EXAMPLE 1-(4) above, to which well (i) 50 μl of anti-human ZAQL-1 antibody solution diluted with Buffer C in 50 ng/ml, (ii) 50 μl of human ZAQL-1 or human ZAQL-2 solution diluted with Buffer C and (iii) 50 μl of HRP-labeled human ZAQL-1 (diluted to 400-fold with Buffer C) obtained in EXAMPLE 1 (3) had been added, followed by reaction at 4° C. for 16 hours. After the reaction, the plate was washed with PBS and the enzyme activity on the anti-mouse immunoglobulin antibody-bound microplate was assayed by the method described in EXAMPLE 1-(4) described above.

The results are shown in Table 1.

It is noted that all antibodies are reactive with human ZAQL-1, but not reactive with human ZAQL-2.

Figure 6:
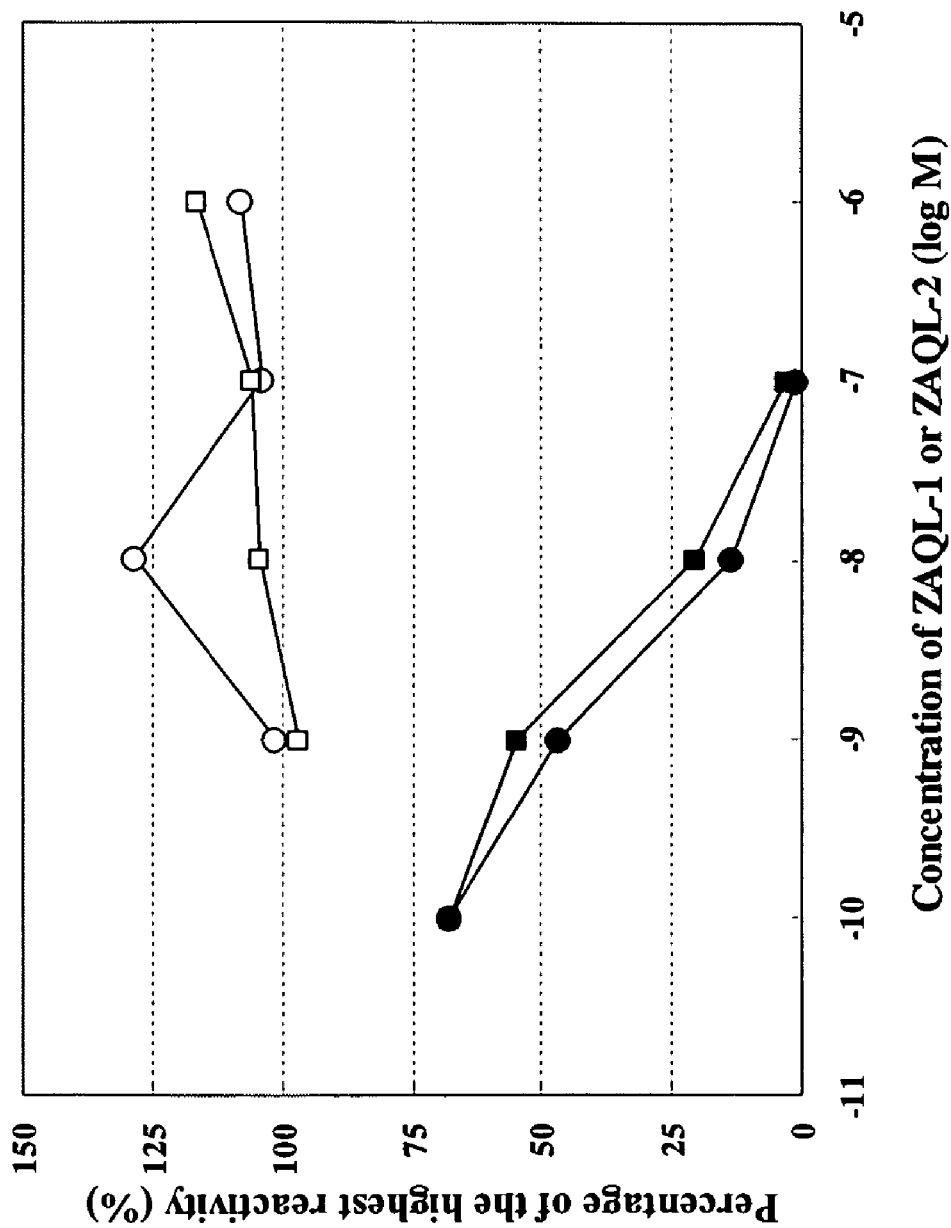
FIG. 6 shows the results of ZL1-107a and ZL1-234a by the competitive assay-EIA. In the figure, -●- (-solid circle-) represents the reactivity of ZL1-107a with ZAQL-1, -○- (-open circle-) represents the reactivity of ZL1-107a with ZAQL-2, -■- (-closed square-) represents the reactivity of ZL1-234a with ZAQL-1 and -□- (-open square-) represents the reactivity of ZL1-234a with ZAQL-2.
Figure 7:
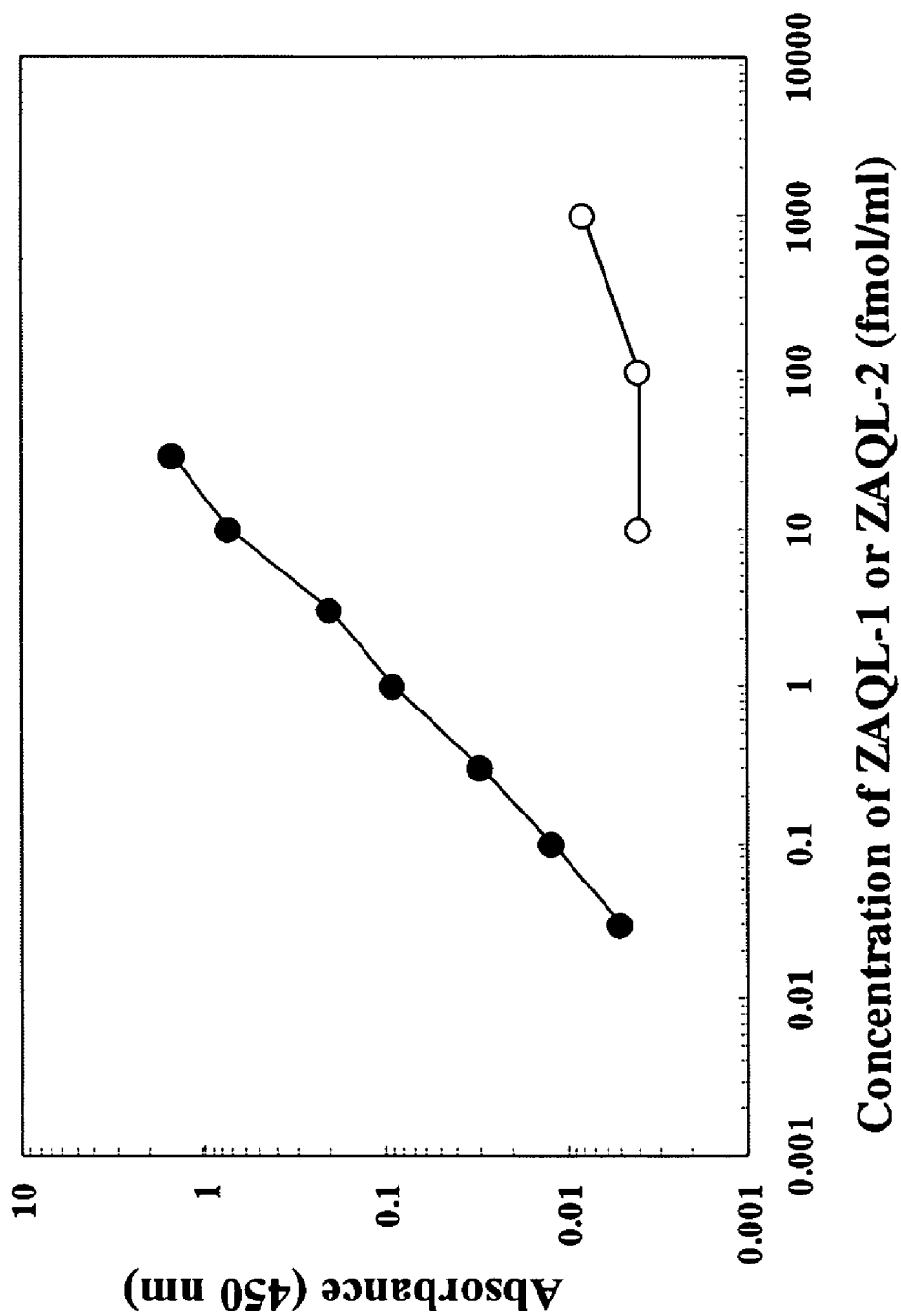
FIG. 7 shows the results of the sandwich assay-EIA using ZL1-107a and ZL1-234a. In the figure, -●- (-solid circle-) represents the reactivity of ZAQL-1 and -○- (-open circle-) represents the reactivity of ZAQL-2.

By way of illustration, the results of monoclonal antibodies ZL1-107a and ZL1-234a by the competitive assay-EIA, which exerted the highest reactivity with human ZAQL-1 in these monoclonal antibodies, are shown in FIG. 6 and FIG. 7.

From the standard curves of ZL1-107a and ZL1-234a for human ZAQL-1, it is noted that the human ZAQL-1 levels providing 0.5 in a percentage of the highest reactivity ($B/B_0$) were 0.8 nM and 1.2 nM, respectively. These results suggest that ZL1-107a and ZL1-234a show high reactivities with human ZAQL-1.

EXAMPLE 3

Preparation of HRP-labeled Anti-ZAQL-1 Monoclonal Antibody (ZL1-234a-HRP)

After 50 μl of DMF containing 0.68 μmol of GMBS was added to 0.1M phosphate buffer (pH 6.8) containing 8.51 mg (56.7 nmol) of the purified fraction of ZL1-234a, the mixture was reacted at room temperature for 40 minutes. The reaction liquid was separated on a Sephadex G-25 column (eluant: 0.1 M phosphate buffer, pH 6.7) to give 5.96 mg of the maleimide-introduced antibody fraction. Next, 60 μl of DMF containing 6.85 μmol of SPDP was added to 1.14 ml of 0.02M phosphate buffer (pH 6.8) containing 18.3 mg (457 nmol) of HRP (further containing 0.15M NaCl), and the mixture was reacted at room temperature for 40 minutes. Subsequently, 0.4 ml of 0.1M acetate buffer (pH 4.5) containing 68.5 μmol of dithiothreitol was added to the mixture. After reacting at room temperature for 20 minutes, the reaction mixture was separated on a Sephadex G-25 column (eluent: 0.1M phosphate buffer containing 2 mM EDTA, pH 6.0) to give 9.8 mg of SH-introduced HRP. Next, 8 mg of the SH-introduced HRP was mixed with 3 mg of the maleimide-introduced antibody fraction. After the mixture was concentrated to about 0.5 ml with Collodion Bag (manufactured by Sartorius K. K.), the concentrate was allowed to stand at 4° C. for 16 hours. The reaction liquid was applied to a Sephacryl S-300HR column (manufactured by Pharmacia), which had been equilibrated with 0.1M phosphate buffer (pH 6.5) to purify the ZL1-234a-HRP complex fraction.

EXAMPLE 4

Sandwich Assay—EIA

After 100 μl each of 0.1M carbonate buffer (pH 9.6 solution) containing 15 μg/ml of the purified monoclonal antibody ZL1-107a obtained in EXAMPLE 1 was dispensed in a 96-well microplate, the plate was allowed to stand at 4° C. for 24 hours. The redundant binding sites in the wells were inactivated by adding 400 μl of Block Ace diluted with PBS to 4-fold.

To the plate prepared as described above, 100 μl each of human ZAQL-1 or human ZAQL-2 standard preparation diluted in 0.02M phosphate buffer (pH 7) containing Buffer C was added, and the mixture was reacted at 4° C. for 24 hours. After washing with PBS, 100 μl of ZL1-234a-HRP (diluted with Buffer C to 10,000-fold) prepared in EXAMPLE 3 above was added to the reaction mixture, followed by reacting at 4° C. for 24 hours. After washing with PBS, the enzyme activity on the solid phase was assayed by the method described in EXAMPLE 1 (4) above, using the TMB microwell peroxidase substrate system (enzyme reaction for 20 minutes).

The results are shown in FIG. 7.

According to this sandwich assay-EIA, human ZAQL-1 could be detected in 0.1 fmol/mL, and any reaction with human ZAQL-2 did not occur to the level of 10001 fmol/mL. Thus, the sandwich assay-EIA using ZL1-107a as a solid phase and ZL1-234a-HRP as a marker can detect human ZAQL-1 with extremely high selectivity and sensitivity.

EXAMPLE 5

Neutralizing Action on the Biological Activity of Human ZAQL-1 by ZL1-107a and ZL1-234a The neutralizing action on human ZAQL-1 by ZL1-107a and ZL1-234a was determined on FLIPR (Molecular Devices, Inc.) using the ZAQ-expressed CHO cells (ZAQC-B1 cells) described in EXAMPLE 3 (5) in WO 02/06483, whereby the intracellular $Ca^{2+}$ ion level-increasing activity was used as an indicator.

The ZAQ-expressed CHO cells were suspended in Dulbecco's modified Eagle medium (DMEM) (Nissui Seiyaku Co., Ltd.) supplemented with 10% dialyzed fetal bovine serum (dFBS) (JRH BIOSCIENCES, Inc.) (10% dFBS-DMEM) in $1.2 \times 10^5$ cells/ml. Using a dispenser, 200 μl each of the suspension was inoculated on a 96-well plate for FLIPR (black plate clear bottom, Coster, Inc.) ($4 \times 10^4$ cells/200 μl/well), followed by incubation at 37° C. overnight in a 5% $CO_2$ incubator. The cells thus incubated were used (hereinafter referred to as the cell plate). Then, 20 ml of FLIPR assay buffer [9.8 g of Nissui HANKS 2 (Nissui Seiyaku Co., Ltd.), 0.35 g of sodium hydrogencarbonate, 4.77 g of HEPES; after adjusting the pH to 7.4 with 6M sodium hydroxide solution, the volume was made 1 L followed by sterilization through a filter], 200 μl of 250 mM Probenecid (SIGMA) and 210 μl of fetal bovine serum (FBS) were mixed. Furthermore, 2 vials (50 μg/vial) of Fluo 3-AM (Dojin Chemical Laboratory, Ltd.) were dissolved in 40 μl of dimethylsulfoxide and 40 μl of 20% Pluronic acid (Molecular Probes, Inc.). The resulting solution was added to H/HBSS-Probenecid-FBS solution composed of 20 ml of H/HBSS [9.8 g of HEPES buffered HANKS' balanced solution (Nissui HANKS 2 (Nissui Seiyaku Co., Ltd.), 0.35 g of sodium hydrogencarbonate, 4.77 g of HEPES; after adjusting the pH to 7.4 with sodium hydroxide solution, followed by sterilization through a filter], 200 μl of 250 mM Probenecid and 200 μl of fetal bovine serum (FBS) and then mixed. After the culture solution was removed using an 8-channel pipette, 100 μl each/well of the mixture was dispensed to the culture medium-removed cell plate, followed by incubation at 37° C. for an hour in a 5% $CO_2$ incubator (dye loading). ZL1-107a and ZL1-234a and, as a control antibody, anti-PrRP monoclonal antibody (P2L-1Ta) (Biochem. Biophys. Res. Commun., 257, 264-268 (1998)) having the same IgG subclass structure (IgG1, κ) as ZL1-107a and ZL1-234a were diluted in 120 μl of Hanks'/HBSS containing 2.5 mM Probenecid and 0.2% BSA. After incubation with human ZAQL-1 ($1 \times 10^{-8}$ M) at 37° C. for an hour, 5 μl of each fraction was transferred to a 96-well plate for FLIPR (V-Bottom Plate, Coster, Inc.) (hereinafter referred to as a sample plate). After completion of the dye loading onto the cell plate, the cell plate was washed 4 times with a wash buffer, which was obtained by adding 2.5 mM Probenecid to Hanks'/HBSS, using a plate washer to leave 100 μl of the wash buffer after the washing. The cell plate and the sample plate were set in FLIPR for the assay (50 μl of a sample from the sample plate was automatically transferred to the cell plate on the FLIPR device).

Figure 8:
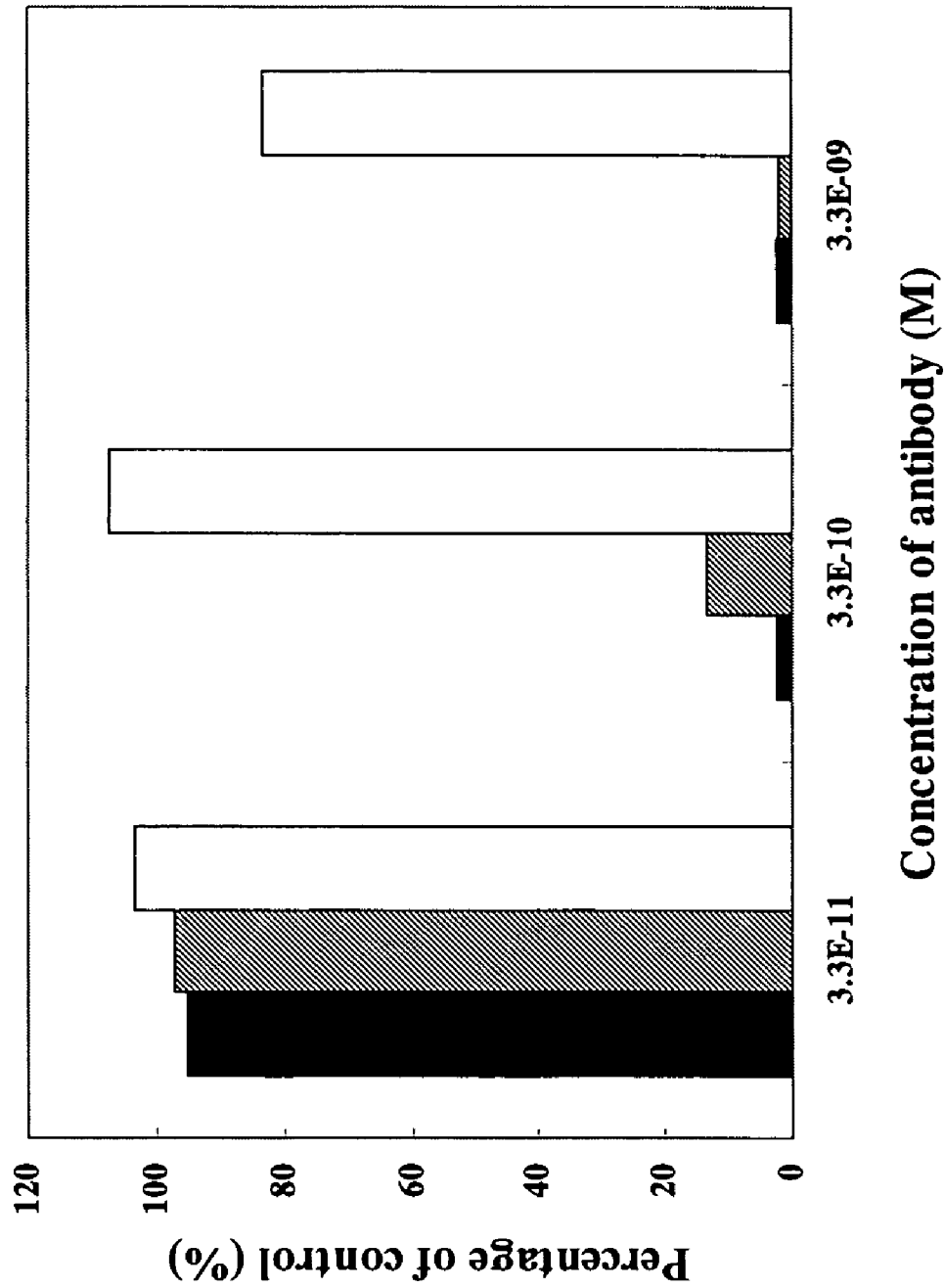
FIG. 8 shows the neutralizing action of ZAQL-1 in the co-presence of ZL1-107a or ZL1-234a or P2L-1Ta on the intracellular $Ca^{2+}$ ion level increasing activity using the ZAQ-expressed CHO cells (ZAQC-B1). In the figure, solid bars represent the percentage of control (without adding any antibody) in the co-presence of ZL1-107a and ZAQL-1 for the intracellular $Ca^{2+}$ ion level increasing activity in the ZAQC-B1 cells, hatched solid bars represent the percentage of control (without adding any antibody) in the co-presence of ZL1-234a and ZAQL-1 for the intracellular $Ca^{2+}$ ion level increasing activity in the ZAQC-B1 cells, and open bars represent the percentage of control (without adding any antibody) in the co-presence of P2L-1Ta and ZAQL-1 for the intracellular $Ca^{2+}$ ion level increasing activity in the ZAQC-B1 cells.

The results are shown in FIG. 8.

The results reveal that ZL1-107a prevented about 97% of the activity of human ZAQL-1 ($3.3 \times 10^{-10}$ M) at $3.3 \times 10^{-10}$ M and prevented about 97% even at $3.3 \times 10^{-9}$ M higher by 10-fold molar concentration. The results also reveal that ZL1-234a prevented about 87% of the activity of human ZAQL-1 ($3.3 \times 10^{-10}$ M) at an equimolar concentration of $3.3 \times 10^{-10}$ M and prevented about 98% even at $3.3 \times 10^{-9}$ M higher by 10-fold molar concentration. On the other hand, the control antibody P2L-1Ta failed to prevent the activity of human ZAQL-1 even at $3.3 \times 10^{-9}$ M, which is a 10-fold higher concentration than human ZAQL-1.

The foregoing results reveal that ZL1-107a and ZL1-234a neutralize the intracellular $Ca^{2+}$ ion level-increasing activity of human ZAQL-1, indicating that these antibodies are usable as neutralizing antibodies.

EXAMPLE 6

Quantification of Human ZAQL-1 in Plasma

Human plasma was diluted to 2-fold with an equal volume of Buffer C and human ZAQL-1 was then quantified by the sandwich assay-EIA described in EXAMPLE 4 described above.

The results are shown in Table 2.

TABLE 2

| Immunological Activity of ZAQL-1 in Human Plasma | | |
|---|---|---|
| No. | Male (fmol/ml) | Female (fmol/ml) |
| 1 | 2.33 | 0.84 |
| 2 | 1.39 | 0.90 |
| 3 | 1.43 | 2.03 |
| 4 | 2.06 | 4.46 |
| 5 | 1.52 | 1.20 |
| 6 | 4.10 | 1.02 |
| 7 | 1.92 | 1.65 |
| 8 | 1.35 | 0.62 |
| 9 | 1.69 | 0.93 |
| 10 | 1.62 | 1.41 |
| 11 | 1.21 | |
| 12 | 1.48 | |

In human plasma (1 ml), human ZAQL-1 was present in:
Male: 1.84 ± 0.23 fmol/ml (mean ± SEM, n = 12)
Female: 1.51 ± 0.35 fmol/ml (mean ± SEM, n = 10)

EXAMPLE 7

Detection of Human ZAQL-1 in Human Plasma by RP-HPLC

To identify the immunological activity of human ZAQL-1 contained in human plasma, which was described in EXAMPLE 6, 20 ml of acetonitrile was added to 10 ml of human plasma, followed by mixing them. The mixture was centrifuged (15,000 rpm, 5 minutes) to remove proteins. After the supernatant was lyophilized, this fraction was concentrated and the concentrate was fractionated on reverse phase HPLC using a column (ODS-80™).

Column Conditions:
Column: ODS-80™ (4.6×250 mm)
Eluents: Eluent A (5% acetonitrile containing 0.05% trifluoroacetic acid)
Eluent B (60% acetonitrile containing 0.05% trifluoroacetic acid)
Elution method: The acetonitrile concentration was increased from 5% to 30% for the initial 5 minutes and then linearly increased to 30-40% over 30 minutes.
Flow rate: 1.0 ml/min.
Fractionation: 0.5 ml/tube The eluted fraction was lyophilized and the lyophilized product was dissolved in 250 μl of Buffer C. The solution was provided for the sandwich assay-EIA described in EXAMPLE 4 above.

Figure 9:
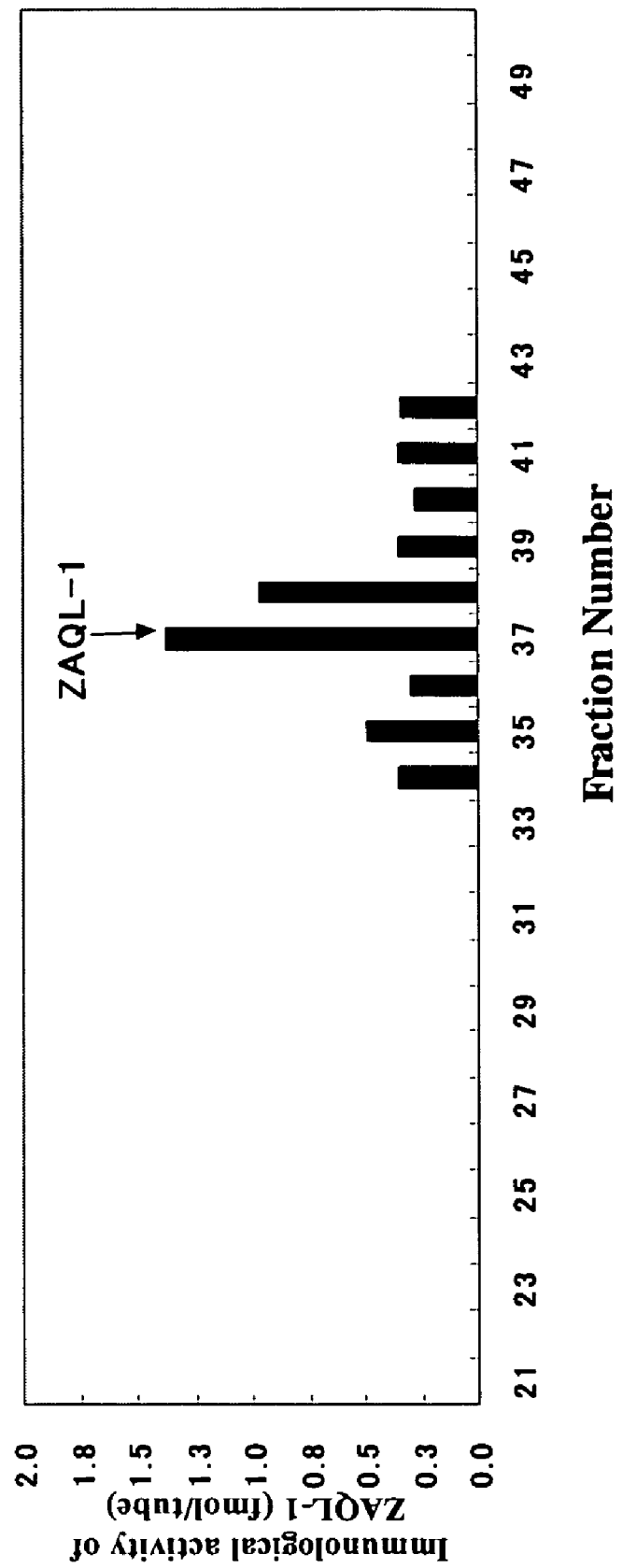
FIG. 9 shows the eluted positions of human ZAQL-1 immunological activity in human plasma fractionated by reversed phase HPLC.

The results are shown in FIG. 9.

The immunological activity of human ZAQL-1 in plasma was detected almost at the eluted positions of human ZAQL-1 (recovery rate of 102%). It was thus confirmed that the sandwich assay-EIA detected human ZAQL-1.

The results indicate that this assay system becomes an important means for studying changes of human ZAQL-1 in plasma.

EXAMPLE 8

Quantification of Human ZAQL-1 in Plasma of Pregnant Women

The plasma of pregnant women collected at each week of gestation was diluted to 2-fold in an equal volume of Buffer C and human ZAQL-1 was quantified by the sandwich assay-EIA described in EXAMPLE 4 above. The plasma of pregnant women was purchased from DCP Corporation, giving the informed consent.

The results are shown in Table 3.

TABLE 3

| No. | 4-13 Weeks (fmol/ml) | 14-27 Weeks (fmol/ml) | 28-40 Weeks (fmol/ml) | Day 5 after Delivery (fmol/ml) |
|---|---|---|---|---|
| 1 | 2.57 | 6.86 | 3.07 | 0.96 |
| 2 | 9.80 | 2.78 | 3.76 | 1.28 |
| 3 | 3.10 | 2.26 | 6.13 | 1.80 |
| 4 | 8.89 | 2.89 | 3.80 | 1.40 |
| 5 | 11.0 | 3.52 | 5.74 | 1.58 |
| 6 | 7.08 | 1.17 | 3.37 | 10.0 |
| 7 | 4.77 | 4.56 | 3.46 | 4.19 |
| 8 | 8.12 | 8.18 | 3.16 | 3.16 |
| 9 | 3.00 | 2.69 | 3.95 | 2.63 |
| 10 | 2.38 | 4.73 | 3.57 | 1.63 |
| 11 | 6.81 | 3.31 | 6.72 | 2. |
| 12 | 8.99 | 3.18 | | |
| 13 | | 5.10 | | |
| 14 | | 7.27 | | |
| 15 | | 1.00 | | |
| 16 | | 16.5 | | |
| Mean | 6.05 | 4.75 | 4.25 | 2.86 |
| SEM | 0.89 | 0.94 | 0.39 | 0.85 |

Table 3 suggests that the human ZAQL-1 level in blood increases at the first trimester (up to 13 weeks of gestation), decreases during the course of pregnancy and reverts to normal level after delivery. When compared to the ZAQL-1 level in the same group of women during the non-pregnancy time ($1.51 \pm 0.35$ fmol/ml), the level increased by about 4.0 times at the first trimester (4 to 13 weeks) and by about 2.8 times even at the third trimester (28 to 40 weeks).

The results reveal that human ZAQL-1 increases its production or secretion during pregnancy. Therefore, human ZAQL-1 level in blood is usable as an indicator of pregnancy and the antibody of the present invention is useful as a clinical diagnostic agent.

EXAMPLE 9

Detection of Human ZAQL-1 in Plasma of Pregnant Women by RP-HPLC

To identify the immunological activity of human ZAQL-1 contained in the plasma of pregnant women, which was described in EXAMPLE 8, 2 ml of acetonitrile was added to 1 ml of the plasma from pregnant women of 11 weeks, followed by mixing them. The mixture was centrifuged (15,000 rpm, 5 minutes) to remove proteins. After the supernatant was lyophilized, this fraction was concentrated and the concentrate was fractionated on reverse phase HPLC using a column (ODS-80™) under the same conditions as in EXAMPLE 7.

The eluted fraction was lyophilized and the lyophilized product was dissolved in 250 μl of Buffer C. The resulting solution was provided for the sandwich assay-EIA described in EXAMPLE 4 above.

Figure 10:
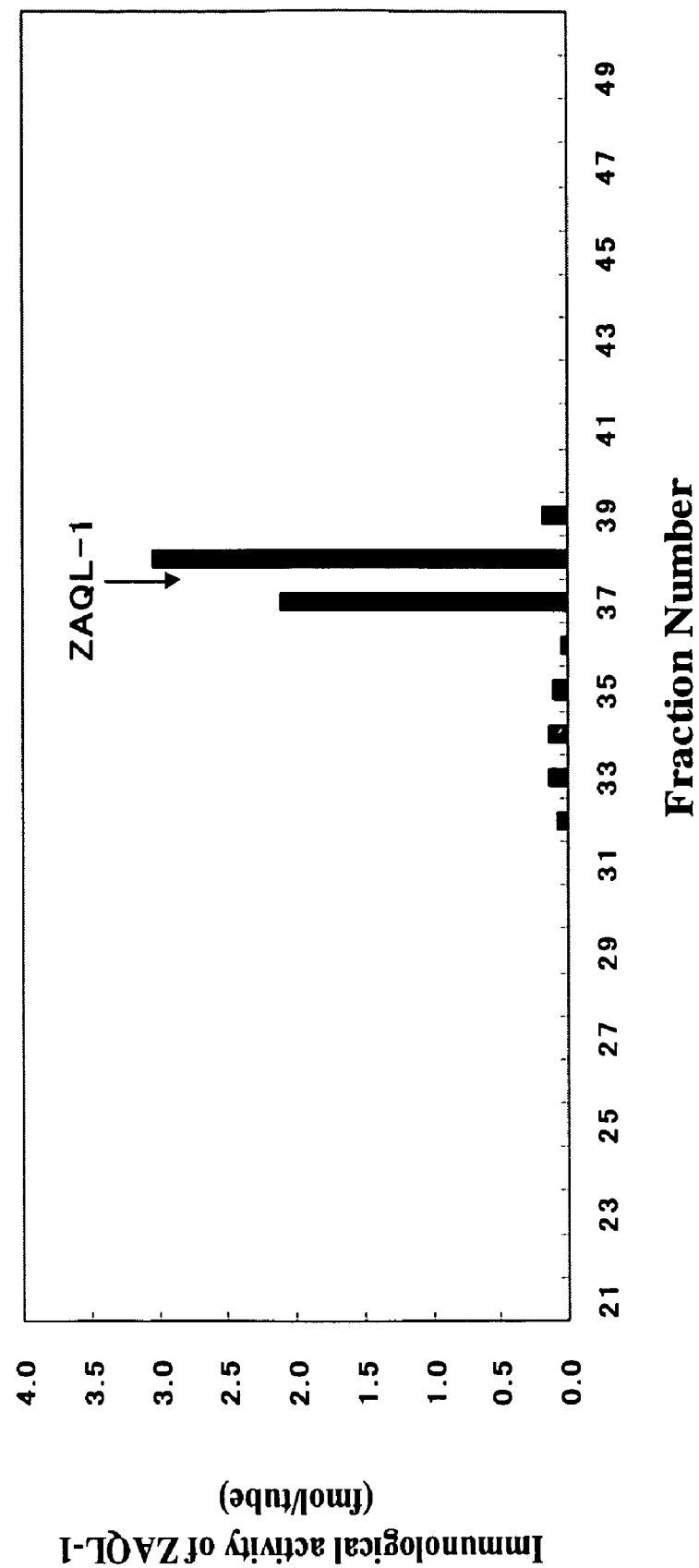
FIG. 10 shows the eluted positions of human ZAQL-1 immunological activity in the plasma of pregnant women fractionated by reversed phase HPLC.

The results are shown in FIG. 10.

The immunological activity of human ZAQL-1 in the plasma of pregnant women was detected almost at the eluted positions of human ZAQL-1 (recovery rate of 70%). It was therefore confirmed that the sandwich assay-EIA detected human ZAQL-1 in the plasma of pregnant women.

The results reveal that the human ZAQL-1 level in plasma increases during pregnancy.

EXAMPLE 10

Quantification of Human ZAQL-1 in Follicular Fluid

The follicular fluid of patients was diluted to 2-fold in an equal volume of Buffer C and human ZAQL-1 was quantified by the sandwich assay-EIA described in EXAMPLE 4 above. The follicular fluid was supplied in the collaborative research with Assistant Professor Usui of the Institute of Obstetrics & Gynecology in Clinical Medicine, University of Tsukuba, giving the informed consent. It was also approved by the ethics committees of University of Tsukuba and Takeda Pharmaceutical Limited.

The results are shown in Table 4.

TABLE 4

| Disease | Endo-metriosis | Ovulation disorders | Endometriosis complicated with ovulation disorders | None of endometriosis or ovulation disorders |
|---|---|---|---|---|
| Case number | 15 | 22 | 9 | 40 |
| ZAQL-1 (fmol/mL) | $116 \pm 23.7$ | $131 \pm 15.8$ | $211 \pm 24.5$ | $122 \pm 12$ |

In the table, values represent mean ± standard error (fmol/mL).

The foregoing results that human ZAQL-1 showed a higher level in the follicular fluid of the patients with complication of endometriosis and ovulation disorders suggested that human ZAQL-1 would be involved in endometrial cancer and endometriosis.

EXAMPLE 11

Detection of Human ZAQL-1 in Follicular Fluid by RP-HPLC

To identify the immunological activity of human ZAQL-1 contained in the follicular fluid, which was described in EXAMPLE 10, 0.9 ml of acetonitrile was added to 0.45 ml of the follicular fluid, followed by mixing them. The mixture was centrifuged (15,000 rpm, 5 minutes) to remove proteins. After the supernatant was lyophilized, this fraction was concentrated and the concentrate was fractionated on reverse phase HPLC using a column (ODS-80™) under the same conditions as in EXAMPLE 7.

The eluted fraction was lyophilized and the lyophilized product was dissolved in 250 µl of Buffer C. The resulting solution was provided for the sandwich assay-EIA described in EXAMPLE 4 above.

Figure 11:
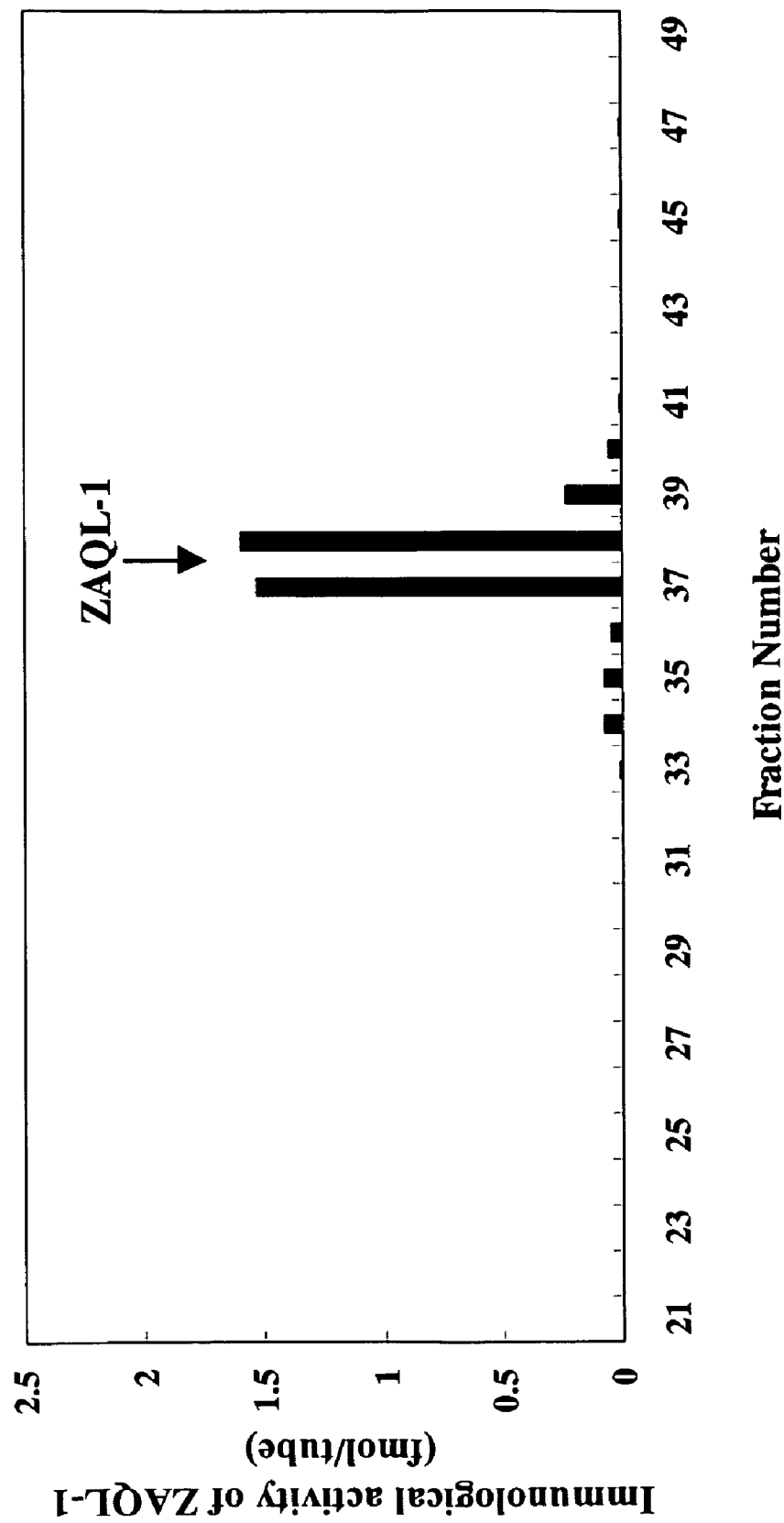
FIG. 11 shows the eluted positions of human ZAQL-1 immunological activity in the follicular fluid fractionated by reversed phase HPLC.

The results are shown in FIG. 11.

The immunological activity of human ZAQL-1 in the follicular fluid was detected almost at the eluted positions of human ZAQL-1 (recovery rate of 70%). It was therefore confirmed that the sandwich assay-EIA detected human ZAQL-1 in the plasma of pregnant women.

INDUSTRIAL APPLICABILITY

The antibody of the present invention has an extremely high binding ability to a polypeptide comprising the amino acid sequence represented by SEQ ID NO: 1 or SEQ ID NO: 2, or a salt thereof, and can neutralize the intracellular $[Ca^{2+}]$ increasing activity of the polypeptide comprising the amino acid sequence represented by SEQ ID NO: 1 or SEQ ID NO: 2, or a salt thereof. By inhibiting the action of the polypeptide comprising the amino acid sequence represented by SEQ ID NO: 1 or SEQ ID NO: 2, or a salt thereof, the antibody is useful as an agent for preventing/treating, e.g., digestive diseases (e.g., enteritis, diarrhea, constipation, malabsorption syndrome, etc.), diseases associated with angiogenesis [e.g., cancers (e.g., thyroid cancer, testicular cancer, adrenal tumor, pancreatic cancer, lung cancer, kidney cancer, liver cancer, non-small cell lung cancer, ovarian cancer, prostate cancer, gastric cancer, bladder cancer, breast cancer, cervical cancer, colonic cancer, rectal cancer, endometrial cancer, etc.), polycystic ovary syndrome, ovarian hyperstimulation syndrome, etc.], diseases relating to pregnancy (e.g., toxemia of pregnancy, placental hypoplasia, threatened abortion, endometriosis, sterility, ovulation disorders, etc.), eating disorders (e.g., anorexia, bulimia nervosa, etc.), sleeping disorders [e.g., primary insomnia, circadian rhythm disorders (e.g., changes in physical conditions caused by three-shift work, time zone change syndrome (jet lag), etc.)], seasonal depression, reproductive dysfunction, endocrine diseases, senile dementia, Alzheimer's disease, various disorders caused by aging, cerebral circulatory disorders (e.g., apoplexy, etc.), head trauma, spinal injury, epilepsy, anxiety, depression, manic depression, schizophrenia, alcoholism, Parkinson's disease, hypertension, arteriosclerosis, arrhythmia, premenstral syndrome, glaucoma, cancer, AIDS, diabetes, etc. Preferably, the antibody is an agent for preventing/treating diseases associated with angiogenesis, diseases relating to pregnancy, etc., and more preferably, an gent for preventing/treating endometrial cancer, endometriosis, ovulation disorders, etc. Furthermore, the antibody can detect a cancer where a polypeptide comprising the amino acid sequence represented by SEQ ID NO: 1 or SEQ ID NO: 2, or a salt thereof is expressed, and thus enables anti-cancer treatment by missile therapy using the antibody of the present invention. According to the immunoassay by the sandwich assay using two kinds of monoclonal antibodies of the present invention, the polypeptide comprising the amino acid sequence represented by SEQ ID NO: 1 or SEQ ID NO: 2, or a salt thereof can be quantified specifically with high sensitivity, and is thus useful for elucidation of the physiological functions of the polypeptide comprising the amino acid sequence represented by SEQ ID NO: 1 or SEQ ID NO: 2, or a salt thereof and pathological conditions. It is also possible to diagnose, e.g., the diseases described above by assaying the blood level of polypeptide comprising the amino acid sequence represented by SEQ ID NO: 1 or SEQ ID NO: 2, or a salt thereof. The antibody of the present invention can also be used for immuno-tissue staining of the polypeptide described above.

The invention claimed is:

1. An isolated monoclonal antibody specifically binding to a polypeptide consisting of the amino acid sequence represented by SEQ ID NO: 1 or SEQ ID NO: 2, or a salt thereof, wherein the monoclonal antibody has an activity of neutralizing an intracellular $Ca^{2+}$ ion level-increasing activity of the polypeptide, wherein the monoclonal antibody does not bind to a polypeptide having the amino acid sequence represented by SEQ ID NO:3, and wherein the monoclonal antibody is ZL1-107a produced from hybridoma ZL1-107 (FERM BP-8256).

2. An isolated monoclonal antibody specifically binding to a polypeptide consisting of the amino acid sequence represented by SEQ ID NO: 1 or SEQ ID NO: 2, or a salt thereof, wherein the monoclonal antibody has an activity of neutralizing an intracellular $Ca^{2+}$ ion level-increasing activity of the polypeptide, wherein the monoclonal antibody does not bind to a polypeptide having the amino acid sequence represented by SEQ ID NO:3, and wherein the monoclonal antibody is ZL1-234a produced from hybridoma ZL1-234 (FERM BP-8257).

3. A hybridoma producing an isolated monoclonal antibody specifically binding to a polypeptide consisting of the amino acid sequence represented by SEQ ID NO: 1 or SEQ ID NO: 2, or a salt thereof, wherein the monoclonal antibody has an activity of neutralizing an intracellular $Ca^{2+}$ ion level-increasing activity of the polypeptide, and the monoclonal antibody does not bind to a polypeptide having the amino acid sequence represented by SEQ ID NO:3, wherein the hybridoma is ZL1-107 (FERM BP-8256) or ZL1-234 (FERM BP-8257).

4. A method of producing the monoclonal antibody ZL1-107a producible from a hybridoma represented by ZL1-107 (FERM BP-8256), or ZL1-234a producible from a hybridoma represented by ZL1-234 (FERM BP-8257) which comprises culturing the hybridoma according to claim 3 in vivo or in vitro and collecting the monoclonal antibody from the body fluid or culture.

5. The monoclonal antibody of claim 1, which is labeled.

6. The monoclonal antibody of claim 2, which is labeled.

* * * * *

UNITED STATES PATENT AND TRADEMARK OFFICE
CERTIFICATE OF CORRECTION

| | | |
|---|---|---|
| PATENT NO. | : 7,662,380 B2 | |
| APPLICATION NO. | : 10/542664 | |
| DATED | : February 16, 2010 | |
| INVENTOR(S) | : Matsumoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 703 days.

Signed and Sealed this

Thirtieth Day of November, 2010

David J. Kappos
*Director of the United States Patent and Trademark Office*

SEQUENCE LISTING

<160> NUMBER OF SEQ ID NOS: 3

<210> SEQ ID NO 1
<211> LENGTH: 86
<212> TYPE: PRT
<213> ORGANISM: Homo sapiens

<400> SEQUENCE: 1

Ala Val Ile Thr Gly Ala Cys Glu Arg Asp Val Gln Cys Gly Ala Gly
 1               5                  10                  15

Thr Cys Cys Ala Ile Ser Leu Trp Leu Arg Gly Leu Arg Met Cys Thr
             20                  25                  30

Pro Leu Gly Arg Glu Gly Glu Glu Cys His Pro Gly Ser His Lys Val
         35                  40                  45

Pro Phe Phe Arg Lys Arg Lys His His Thr Cys Pro Cys Leu Pro Asn
     50                  55                  60

Leu Leu Cys Ser Arg Phe Pro Asp Gly Arg Tyr Arg Cys Ser Met Asp
 65                  70                  75                  80

```
Leu Lys Asn Ile Asn Phe
                85

<210> SEQ ID NO 2
<211> LENGTH: 86
<212> TYPE: PRT
<213> ORGANISM: Homo sapiens

<400> SEQUENCE: 2

Ala Val Ile Thr Gly Ala Cys Glu Arg Asp Val Gln Cys Gly Ala Gly
                5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Ile
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
                85

<210> SEQ ID NO 3
<211> LENGTH: 81
<212> TYPE: PRT
<213> ORGANISM: Homo sapiens

<400> SEQUENCE: 3

Ala Val Ile Thr Gly Ala Cys Asp Lys Asp Ser Gln Cys Gly Gly Gly
                5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Val
        35                  40                  45

Pro Phe Phe Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Gln
65                  70                  75                  80

Lys
```